(12) United States Patent
Beyaert et al.

(10) Patent No.: US 7,414,026 B2
(45) Date of Patent: Aug. 19, 2008

(54) INHIBITORS OF NF-KAPPAB ACTIVATION

(75) Inventors: Rudi Beyaert, Zingem (BE); Karen Heyninck, Sint-Martens-Latem (BE); Walter Fiers, Destelbergen (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 361 days.

(21) Appl. No.: 10/680,998

(22) Filed: Oct. 8, 2003

(65) Prior Publication Data

US 2004/0092430 A1    May 13, 2004

Related U.S. Application Data

(60) Division of application No. 09/702,953, filed on Oct. 31, 2000, now Pat. No. 6,673,897, which is a continuation of application No. PCT/BE99/00055, filed on May 5, 1999.

(51) Int. Cl.
*A61K 38/00* (2006.01)
(52) U.S. Cl. ..................................................... 514/12
(58) Field of Classification Search .................. 514/12
See application file for complete search history.

(56) References Cited

U.S. PATENT DOCUMENTS

| | | | |
|---|---|---|---|
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter et al. |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |

FOREIGN PATENT DOCUMENTS

| | | |
|---|---|---|
| WO | WO 91/16024 | 10/1991 |
| WO | WO 91/17424 | 11/1991 |
| WO | WO 93/24641 | 12/1993 |
| WO | WO 97/37016 | 10/1997 |
| WO | WO 99/57133 | 11/1999 |

OTHER PUBLICATIONS

Song et al., The tumor necrosis factor-inducible zinc finger protein A20 interacts with TRAF1/TRAF2 and inhibits NF-kB activation, Proc. Natl. Acad. Sci. USA, 1996, vol. 93, p. 6721-6725.*
Jaattela et al., A20 zzzzzinc finger protein inhibits YNF and IL-1 signaling, The Journal of Immunology, 1996, 156, p. 1166-1173.*
Ferran et al., A29 inhibits NF-kB activation in endothelial cells without sesnsitizing to tumor necrosis factor-mediated apoptosis, Blood, 1998, vol. 91, p. 2249-2258.*
Heyninck et al., The zinck finger protein A20 inhibits TNF-induced NF-kB-dependent gene expression by interfering with an RIP- or TRAF2-mediated transactivation signal and directly binds to a novel NF-kB-inhibiting protein ABIN, The Journal of Cell Biology, 1999, vol. 145, p. 1471-1482.*
De Valck et al., "A20, an inhibitor of cell death, self-associates by its zinc finger domain," 384 FEBS Letters 61-64 (1996).
Fukushi, M., Homosapiens mRNA for HIV-1, Nef-associated factor 1 beta (Naf1 bets),: EMHUM Database Entry HSA011896, Accession No. AJ011896, Oct. 14, 1998, XP002124741.
Fukushi, M., et al., "NAF1 alpha protein (KIAA0113 protein)," TREMBL Database Entry A15025, Accession No. Q15025, Nov. 1, 1996, XP02124740.
Hendrick, B.D., et al., "An X-linked homologue of the autosomal imprinted gene NF127 escapes X chromosome inactivation," EMHUM Database Entry HS4131510; Accession No. U41315, May 19, 1996, XP002125387.
Heyninck et al., "The Zinc Finger Protein A20 Inhibits TNF-induced NF-kB-dependent Gene Exp[ression by interfering with an RIP- or TRAF2-mediated Transactivation Signal and Directly Binds to a Novel NF-kB-inhibiting Protein ABIN," 145 The Journal of Cell Biology 1471-1482 (1999).
Miyajima, N., et al., "Human mRNA for KIAA 0133 gene, partial coding sequence," EMHUM Databse Entry HSORFA2, Accession No. D30755, May 21, 1994, XP002124739.
Nomura et al., "mRNA for ORF, partial CDS (fragment)," TRHUM Database Entry Q15025; Nov. 1, 1996, Accession No. Q15025, XP002080989.
Song et al., "The tumor necrosis factor-inducible zinc finger protein A20 interacts with TRAF1/TRAF2 and inhibits NF-kB activation," 93 Proc. Natl. Acad. Sci. USA 6721-6725 (1996).
Yen, R.W.C., et al., "DNA-methyltransferase," SWISSPROT Database Entry MTDM_Human; May 1, 1992, Accession No. P26358, XP002080990.
PCT International Search Report, PCT/BE99/00055, dated Dec. 31, 1999 (9 pages).
PCT International Preliminary Examination Report, PCT/BE99/00055, dated Aug. 10, 2000.

(Continued)

*Primary Examiner*—Karen Cochrane Carlson
*Assistant Examiner*—Agnes B. Rooke
(74) *Attorney, Agent, or Firm*—TraskBritt

(57) ABSTRACT

The present invention relates to novel inhibitors of the Nuclear factor kappa B (NF-κB) activating pathway useful in the treatment of NF-κB related diseases and/or in the improvement of anti-tumor treatments. These inhibitors interfere early in the TRAF induced signaling pathway and are therefore more specific than IκB.

6 Claims, 10 Drawing Sheets

OTHER PUBLICATIONS

Yamamoto et al., "Therapeutic potential of inhibition of the NF-kappaB pathway in the treatment of inflammation and cancer," 107(2) J. Clin. Invest. 135-142 (Jan. 2001).

Ghosh, et al., "Missing Pieces in the NF-kappaB Puzzle," 109 Cell S81-S96 (Apr. 2002).

Baldwin, A.S., "The transcription factor NF-kappaB and human disease," 107(1) J. Clin. Invest. 3-6 (Jan. 2001).

Ngo et al., "Computational Complexity, Protein Structure Prediction and the Levinthal Paradox," The Protein Folding Problem and Tertiary Structure, Merz et al. ed., pp. 14-16 (1994).

Zhang, et al., "Environment-dependent residue contact energies for proteins," 97(6) Proc. Natl. Sci. 2550-2555 (Mar. 2000).

Fukushi et al., (Nov. 1, 1996) Acc. No. Q15025, SPTREMBL_17 database, GenCore Version 4.5, Accessed May 8, 2002.

Gupta, et al. (Mar. 1, 2001) Acc. No. Q9H1J3, SPTREMBL_17, GenCore Version 4.5, Accessed May 8, 2002.

Heyninck, K., et al., "Structure-function analysis of the A20-binding inhibitor of NF-κB activation, ABIN-1," 536 FEBS Letters 135-140 (2003).

Wullaert et al., LIND/ABIN-3 Is a Novel Lipopolysaccharide-inducible Inhibitor of NF-kappaB Activation, The Journal of Biological Chemistry, Jan. 5, 2007, pp. 81-90, vol. 282, No. 1.

\* cited by examiner

SEQUENCE LISTING

```
<160> NUMBER OF SEQ ID NOS: 19

<210> SEQ ID NO 1
<211> LENGTH: 2812
<212> TYPE: DNA
<213> ORGANISM: Mus musculus
<220> FEATURE:
<221> NAME/KEY: Intron
<222> LOCATION: (81)..(116)
<220> FEATURE:
<221> NAME/KEY: CDS
```

<222> LOCATION: (117)..(2060)

<400> SEQUENCE: 1

| | |
|---|---|
| cacagggagg catggccgca ctcactgggc acatcttcag atcacctcgt gcattctcgg | 60 |
| atgagtgacc tgggctgaag ctaggcggcc gtcacggcag gggttgagcc accctc atg<br>                                                                                                                                                                                      Met<br>                                                                                                                                                                                       1 | 119 |

```
gaa ggg aga gga ccc tac cgg atc tac gac cca ggg ggc agc acg cct      167
Glu Gly Arg Gly Pro Tyr Arg Ile Tyr Asp Pro Gly Gly Ser Thr Pro
            5                  10                  15 ctg gga gag gtg tcc gca gct ttt gaa cgt cta gtg gag gag aat act      215
Leu Gly Glu Val Ser Ala Ala Phe Glu Arg Leu Val Glu Glu Asn Thr
 20                  25                  30 cgg ctg aag gga aaa atg caa ggg ata aag atg tta ggg gag ctt ctg      263
Arg Leu Lys Gly Lys Met Gln Gly Ile Lys Met Leu Gly Glu Leu Leu
         35                  40                  45 gag gag tct cag atg gaa gcg tcc aga ctc cgg cag aag gca gag gag      311
Glu Glu Ser Gln Met Glu Ala Ser Arg Leu Arg Gln Lys Ala Glu Glu
 50                  55                  60                  65 ctg gtc aag gac agc gag ctg tca cca ccg aca tct gcc ccc tcc ttg      359
Leu Val Lys Asp Ser Glu Leu Ser Pro Pro Thr Ser Ala Pro Ser Leu
                 70                  75                  80 gtc tcc ttt gat gac ctg gct gag ctc aca gga cag gat aca aag gtc      407
Val Ser Phe Asp Asp Leu Ala Glu Leu Thr Gly Gln Asp Thr Lys Val
             85                  90                  95 cag gta cat cct gct acc agc act gcc gcc acc acc acc gcc acc gcc      455
Gln Val His Pro Ala Thr Ser Thr Ala Ala Thr Thr Thr Ala Thr Ala
        100                 105                 110 acc acg gga aac tcc atg gag aag ccc gag cca gcc tcc aaa tct ccg      503
Thr Thr Gly Asn Ser Met Glu Lys Pro Glu Pro Ala Ser Lys Ser Pro
    115                 120                 125 tcc aat ggc gcc tcc tcg gac ttt gaa gtg gtc cct act gag gag cag      551
Ser Asn Gly Ala Ser Ser Asp Phe Glu Val Val Pro Thr Glu Glu Gln
130                 135                 140                 145 aat tca ccc gaa act ggc agc cac cct acg aac atg atg gac ctg ggg      599
Asn Ser Pro Glu Thr Gly Ser His Pro Thr Asn Met Met Asp Leu Gly
                150                 155                 160 ccc cca ccc cca gag gac agc aac ctg aag ctc cac ctg cag cgc ctg      647
Pro Pro Pro Pro Glu Asp Ser Asn Leu Lys Leu His Leu Gln Arg Leu
            165                 170                 175 gag acc acc ctt agc gtg tgt gca gag gag cca gac cac agc cag ctc      695
Glu Thr Thr Leu Ser Val Cys Ala Glu Glu Pro Asp His Ser Gln Leu
        180                 185                 190 ttc acc cac ctg ggc cgc atg gcc ctc gag ttc aac agg ttg gcc tcc      743
Phe Thr His Leu Gly Arg Met Ala Leu Glu Phe Asn Arg Leu Ala Ser
    195                 200                 205 aaa gtg cat aaa aat gag cag cgc acc tcc atc ctg cag acc tta tgt      791
Lys Val His Lys Asn Glu Gln Arg Thr Ser Ile Leu Gln Thr Leu Cys
210                 215                 220                 225 gag cag ctg cgc cag gag aat gaa gcc ctg aag gcc aag ctg gac aag      839
Glu Gln Leu Arg Gln Glu Asn Glu Ala Leu Lys Ala Lys Leu Asp Lys
                230                 235                 240 ggc ctg gaa cag cgg gat ctg gct gct gag agg ctg cgg gag gaa aac      887
Gly Leu Glu Gln Arg Asp Leu Ala Ala Glu Arg Leu Arg Glu Glu Asn
            245                 250                 255 acg gag ctc aag aaa ctg ttg atg aac agc agc tgc aaa gag gga ctc      935
Thr Glu Leu Lys Lys Leu Leu Met Asn Ser Ser Cys Lys Glu Gly Leu
        260                 265                 270 tgt ggg cag ccc agc tcc cca aag cca gag ggt gct ggc aag aag ggc      983
```

```
                Cys Gly Gln Pro Ser Ser Pro Lys Pro Glu Gly Ala Gly Lys Lys Gly
                275                 280                 285 gtg gct gga cag cag cag gcc agt gtg atg gcg agt aaa gtc cct gaa         1031
Val Ala Gly Gln Gln Gln Ala Ser Val Met Ala Ser Lys Val Pro Glu
290                 295                 300                 305 gcg ggg gcc ttt gga gca gct gag aag aaa gtg aag ttg cta gaa cag         1079
Ala Gly Ala Phe Gly Ala Ala Glu Lys Lys Val Lys Leu Leu Glu Gln
                310                 315                 320 caa cgc atg gag ctg ctg gaa gtg aac aag cag tgg gac cag cat ttc         1127
Gln Arg Met Glu Leu Leu Glu Val Asn Lys Gln Trp Asp Gln His Phe
            325                 330                 335 cgg tcc atg aag cag cag tat gag cag aag atc aca gag ctt cgc cag         1175
Arg Ser Met Lys Gln Gln Tyr Glu Gln Lys Ile Thr Glu Leu Arg Gln
        340                 345                 350 aag ctg gtg gac ctg cag aaa cag gta act gag ctg gag gcc gaa cgg         1223
Lys Leu Val Asp Leu Gln Lys Gln Val Thr Glu Leu Glu Ala Glu Arg
    355                 360                 365 gag cag aag cag cgt gac ttt gac cgg aaa ctc ctc ctg gcc aaa tcg         1271
Glu Gln Lys Gln Arg Asp Phe Asp Arg Lys Leu Leu Leu Ala Lys Ser
370                 375                 380                 385 aag ata gag atg gaa gag acc gac aag gag cag ctg aca gca gag gcc         1319
Lys Ile Glu Met Glu Glu Thr Asp Lys Glu Gln Leu Thr Ala Glu Ala
                390                 395                 400 aag gaa ctg cgc cag aag gtc agg tac cta cag gat cag ctg agc ccg         1367
Lys Glu Leu Arg Gln Lys Val Arg Tyr Leu Gln Asp Gln Leu Ser Pro
            405                 410                 415 ctc aca agg caa cga gaa tac cag gag aag gag atc cag cgg ctc aat         1415
Leu Thr Arg Gln Arg Glu Tyr Gln Glu Lys Glu Ile Gln Arg Leu Asn
        420                 425                 430 aag gcc ctg gag gag gcc ctc agc atc cag gcc tct cca tca tct ccg         1463
Lys Ala Leu Glu Glu Ala Leu Ser Ile Gln Ala Ser Pro Ser Ser Pro
    435                 440                 445 cct gca gct ttt ggg agt cca gaa ggc gtt ggg ggc cat ctg agg aag         1511
Pro Ala Ala Phe Gly Ser Pro Glu Gly Val Gly Gly His Leu Arg Lys
450                 455                 460                 465 cag gaa cta gtg aca cag aat gag ttg ctg aaa cag cag gta aag atc         1559
Gln Glu Leu Val Thr Gln Asn Glu Leu Leu Lys Gln Gln Val Lys Ile
                470                 475                 480 ttt gaa gag gac ttc cag agg gaa cgg agt gac cgt gaa cgc atg aat         1607
Phe Glu Glu Asp Phe Gln Arg Glu Arg Ser Asp Arg Glu Arg Met Asn
            485                 490                 495 gaa gag aag gag gag ctg aag aag caa gta gag aag ctg cag gcc cag         1655
Glu Glu Lys Glu Glu Leu Lys Lys Gln Val Glu Lys Leu Gln Ala Gln
        500                 505                 510 gtc acc ctg act aat gcc cag ctc aaa act ctc aaa gag gag gag aag         1703
Val Thr Leu Thr Asn Ala Gln Leu Lys Thr Leu Lys Glu Glu Glu Lys
    515                 520                 525 gcc aag gaa gcc ctc aaa cag cag aag agg aaa gca aag gct tcg gga         1751
Ala Lys Glu Ala Leu Lys Gln Gln Lys Arg Lys Ala Lys Ala Ser Gly
530                 535                 540                 545 gag cgc tac cac atg gaa ccc cac cct gag cac gtc tgc ggc gcc tat         1799
Glu Arg Tyr His Met Glu Pro His Pro Glu His Val Cys Gly Ala Tyr
                550                 555                 560 ccc tat gcc tac cca ccc atg cca gcc atg gta cct cac cat gcc tac         1847
Pro Tyr Ala Tyr Pro Pro Met Pro Ala Met Val Pro His His Ala Tyr
            565                 570                 575 aag gac tgg tcc cag atc cga tac cct cca ccc cct gtg ccc atg gag         1895
Lys Asp Trp Ser Gln Ile Arg Tyr Pro Pro Pro Val Pro Met Glu
        580                 585                 590
```

```
cac ccg ccc cca cac ccc aac tct cgc ctc ttc cat ctg ccg gag tac    1943
His Pro Pro Pro His Pro Asn Ser Arg Leu Phe His Leu Pro Glu Tyr
    595                 600                 605 acc tgg cgt cca ccc tgt gca ggg att cgg aat cag agc tct caa gtg    1991
Thr Trp Arg Pro Pro Cys Ala Gly Ile Arg Asn Gln Ser Ser Gln Val
610                 615                 620                 625 atg gac ccg ccc cca gac agg cct gca gag cca gag tct gca gac aat    2039
Met Asp Pro Pro Pro Asp Arg Pro Ala Glu Pro Glu Ser Ala Asp Asn
                630                 635                 640 gac tgt gat ggg ccc cag tga ggctgcagtg ggtcatttgg ttccacttc        2090
Asp Cys Asp Gly Pro Gln
                645 atctttcaga gccagctgac ctcagattgc caaaagtttg aaggccatgt gcatgttctg  2150
tgtgacccaa gccttggcag aggagaggct gggatgggta gctggctcac atccccagcc  2210
aagcctcgaa ctgttgacaa gaccaggag aatccaccca tgggcgccca ccaggttctt   2270
atggatgcaa gcaggagaag ctcaacaccc tgcctcttgc aagacaagg aagcctcacc   2330
tggctttgac ctgccatccg ttgctgaggc cactggcttc atcctaaga atgaggtgca   2390
acaagacccc attctcacag aacctcaaag acttggttcc aggctctcca gagaccatac  2450
ccaactcatg tgcatgtgcc gttttttgctt caagctcagt agcaggacct gccccgagcc  2510
ccctgctcct tgcccctctg tgaggagtta cggagagggc tttgtctcta gagcagaaga  2570
gaatgatggg acggcctgat gctgtcatgc tctccactgc acctgtggca gcctcctgag  2630
agccaccaag atctgggatg aaggccacac cagccatgtc tgctgaaggg ccccagactg  2690
agatgactcc ggcctccaca gttagatgtt tatggtgcca gaggtctata ttaaggtagc  2750
tgtctgttgc taggcagccg tttgcacaaa tcttggacat aaatccaact tgaagatcaa  2810
aa                                                                  2812

<210> SEQ ID NO 2
<211> LENGTH: 647
<212> TYPE: PRT
<213> ORGANISM: Mus musculus

<400> SEQUENCE: 2

Met Glu Gly Arg Gly Pro Tyr Arg Ile Tyr Asp Pro Gly Gly Ser Thr
1               5                   10                  15

Pro Leu Gly Glu Val Ser Ala Ala Phe Glu Arg Leu Val Glu Glu Asn
            20                  25                  30

Thr Arg Leu Lys Gly Lys Met Gln Gly Ile Lys Met Leu Gly Glu Leu
        35                  40                  45

Leu Glu Glu Ser Gln Met Glu Ala Ser Arg Leu Arg Gln Lys Ala Glu
    50                  55                  60

Glu Leu Val Lys Asp Ser Glu Leu Ser Pro Pro Thr Ser Ala Pro Ser
65                  70                  75                  80

Leu Val Ser Phe Asp Asp Leu Ala Glu Leu Thr Gly Gln Asp Thr Lys
                85                  90                  95

Val Gln Val His Pro Ala Thr Ser Thr Ala Ala Thr Thr Thr Ala Thr
            100                 105                 110

Ala Thr Thr Gly Asn Ser Met Glu Lys Pro Glu Pro Ala Ser Lys Ser
        115                 120                 125

Pro Ser Asn Gly Ala Ser Ser Asp Phe Glu Val Val Pro Thr Glu Glu
    130                 135                 140

Gln Asn Ser Pro Glu Thr Gly Ser His Pro Thr Asn Met Met Asp Leu
145                 150                 155                 160
```

```
Gly Pro Pro Pro Pro Glu Asp Ser Asn Leu Lys Leu His Leu Gln Arg
                165                 170                 175
Leu Glu Thr Thr Leu Ser Val Cys Ala Glu Glu Pro Asp His Ser Gln
            180                 185                 190
Leu Phe Thr His Leu Gly Arg Met Ala Leu Glu Phe Asn Arg Leu Ala
        195                 200                 205
Ser Lys Val His Lys Asn Glu Gln Arg Thr Ser Ile Leu Gln Thr Leu
    210                 215                 220
Cys Glu Gln Leu Arg Gln Glu Asn Glu Ala Leu Lys Ala Lys Leu Asp
225                 230                 235                 240
Lys Gly Leu Glu Gln Arg Asp Leu Ala Ala Glu Arg Leu Arg Glu Glu
                245                 250                 255
Asn Thr Glu Leu Lys Lys Leu Leu Met Asn Ser Ser Cys Lys Glu Gly
            260                 265                 270
Leu Cys Gly Gln Pro Ser Ser Pro Lys Pro Glu Gly Ala Gly Lys Lys
        275                 280                 285
Gly Val Ala Gly Gln Gln Ala Ser Val Met Ala Ser Lys Val Pro
    290                 295                 300
Glu Ala Gly Ala Phe Gly Ala Ala Glu Lys Lys Val Lys Leu Leu Glu
305                 310                 315                 320
Gln Gln Arg Met Glu Leu Leu Glu Val Asn Lys Gln Trp Asp Gln His
                325                 330                 335
Phe Arg Ser Met Lys Gln Gln Tyr Glu Gln Lys Ile Thr Glu Leu Arg
            340                 345                 350
Gln Lys Leu Val Asp Leu Gln Lys Gln Val Thr Glu Leu Glu Ala Glu
        355                 360                 365
Arg Glu Gln Lys Gln Arg Asp Phe Asp Arg Lys Leu Leu Leu Ala Lys
    370                 375                 380
Ser Lys Ile Glu Met Glu Glu Thr Asp Lys Glu Gln Leu Thr Ala Glu
385                 390                 395                 400
Ala Lys Glu Leu Arg Gln Lys Val Arg Tyr Leu Gln Asp Gln Leu Ser
                405                 410                 415
Pro Leu Thr Arg Gln Arg Glu Tyr Gln Glu Lys Glu Ile Gln Arg Leu
            420                 425                 430
Asn Lys Ala Leu Glu Glu Ala Leu Ser Ile Gln Ala Ser Pro Ser Ser
        435                 440                 445
Pro Pro Ala Ala Phe Gly Ser Pro Gly Val Gly Gly His Leu Arg
    450                 455                 460
Lys Gln Glu Leu Val Thr Gln Asn Glu Leu Leu Lys Gln Gln Val Lys
465                 470                 475                 480
Ile Phe Glu Glu Asp Phe Gln Arg Glu Arg Ser Asp Arg Glu Arg Met
                485                 490                 495
Asn Glu Glu Lys Glu Glu Leu Lys Lys Gln Val Glu Lys Leu Gln Ala
            500                 505                 510
Gln Val Thr Leu Thr Asn Ala Gln Leu Lys Thr Leu Lys Glu Glu Glu
        515                 520                 525
Lys Ala Lys Glu Ala Leu Lys Gln Gln Lys Arg Lys Ala Lys Ala Ser
    530                 535                 540
Gly Glu Arg Tyr His Met Glu Pro His Pro Glu His Val Cys Gly Ala
545                 550                 555                 560
Tyr Pro Tyr Ala Tyr Pro Pro Met Pro Ala Met Val Pro His His Ala
                565                 570                 575
```

```
Tyr Lys Asp Trp Ser Gln Ile Arg Tyr Pro Pro Pro Val Pro Met
            580                 585                 590

Glu His Pro Pro His Pro Asn Ser Arg Leu Phe His Leu Pro Glu
        595                 600                 605

Tyr Thr Trp Arg Pro Pro Cys Ala Gly Ile Arg Asn Gln Ser Ser Gln
    610                 615                 620

Val Met Asp Pro Pro Asp Arg Pro Ala Glu Pro Glu Ser Ala Asp
625                 630                 635                 640

Asn Asp Cys Asp Gly Pro Gln
                645

<210> SEQ ID NO 3
<211> LENGTH: 627
<212> TYPE: PRT
<213> ORGANISM: Mus musculus

<400> SEQUENCE: 3

Val Ser Ala Ala Phe Glu Arg Leu Val Glu Asn Thr Arg Leu Lys
1               5                   10                  15

Gly Lys Met Gln Gly Ile Lys Met Leu Gly Glu Leu Leu Glu Glu Ser
            20                  25                  30

Gln Met Glu Ala Ser Arg Leu Arg Gln Lys Ala Glu Glu Leu Val Lys
            35                  40                  45

Asp Ser Glu Leu Ser Pro Pro Thr Ser Ala Pro Ser Leu Val Ser Phe
        50                  55                  60

Asp Asp Leu Ala Glu Leu Thr Gly Gln Asp Thr Lys Val Gln Val His
65                  70                  75                  80

Pro Ala Thr Ser Thr Ala Ala Thr Thr Thr Ala Thr Ala Thr Thr Gly
                85                  90                  95

Asn Ser Met Glu Lys Pro Glu Pro Ala Ser Lys Ser Pro Ser Asn Gly
            100                 105                 110

Ala Ser Ser Asp Phe Glu Val Val Pro Thr Glu Glu Gln Asn Ser Pro
            115                 120                 125

Glu Thr Gly Ser His Pro Thr Asn Met Met Asp Leu Gly Pro Pro Pro
        130                 135                 140

Pro Glu Asp Ser Asn Leu Lys Leu His Leu Gln Arg Leu Glu Thr Thr
145                 150                 155                 160

Leu Ser Val Cys Ala Glu Pro Asp His Ser Gln Leu Phe Thr His
                165                 170                 175

Leu Gly Arg Met Ala Leu Glu Phe Asn Arg Leu Ala Ser Lys Val His
            180                 185                 190

Lys Asn Glu Gln Arg Thr Ser Ile Leu Gln Thr Leu Cys Glu Gln Leu
            195                 200                 205

Arg Gln Glu Asn Glu Ala Leu Lys Ala Lys Leu Asp Lys Gly Leu Glu
        210                 215                 220

Gln Arg Asp Leu Ala Ala Glu Arg Leu Arg Glu Asn Thr Glu Leu
225                 230                 235                 240

Lys Lys Leu Leu Met Asn Ser Ser Cys Lys Glu Gly Leu Cys Gly Gln
                245                 250                 255

Pro Ser Ser Pro Lys Pro Glu Gly Ala Gly Lys Lys Val Ala Gly
            260                 265                 270

Gln Gln Gln Ala Ser Val Met Ala Ser Lys Val Pro Glu Ala Gly Ala
            275                 280                 285

Phe Gly Ala Ala Glu Lys Lys Val Lys Leu Leu Glu Gln Gln Arg Met
        290                 295                 300
```

```
Glu Leu Leu Glu Val Asn Lys Gln Trp Asp Gln His Phe Arg Ser Met
305                 310                 315                 320

Lys Gln Gln Tyr Glu Gln Lys Ile Thr Glu Leu Arg Gln Lys Leu Val
                325                 330                 335

Asp Leu Gln Lys Gln Val Thr Glu Leu Glu Ala Glu Arg Glu Gln Lys
            340                 345                 350

Gln Arg Asp Phe Asp Arg Lys Leu Leu Ala Lys Ser Lys Ile Glu
        355                 360                 365

Met Glu Glu Thr Asp Lys Glu Gln Leu Thr Ala Glu Ala Lys Glu Leu
    370                 375                 380

Arg Gln Lys Val Arg Tyr Leu Gln Asp Gln Leu Ser Pro Leu Thr Arg
385                 390                 395                 400

Gln Arg Glu Tyr Gln Glu Lys Glu Ile Gln Arg Leu Asn Lys Ala Leu
                405                 410                 415

Glu Glu Ala Leu Ser Ile Gln Ala Ser Pro Ser Ser Pro Ala Ala
            420                 425                 430

Phe Gly Ser Pro Glu Gly Val Gly Gly His Leu Arg Lys Gln Glu Leu
        435                 440                 445

Val Thr Gln Asn Glu Leu Leu Lys Gln Gln Val Lys Ile Phe Glu Glu
    450                 455                 460

Asp Phe Gln Arg Glu Arg Ser Asp Arg Glu Arg Met Asn Glu Glu Lys
465                 470                 475                 480

Glu Glu Leu Lys Lys Gln Val Glu Lys Leu Gln Ala Gln Val Thr Leu
                485                 490                 495

Thr Asn Ala Gln Leu Lys Thr Leu Lys Glu Glu Lys Ala Lys Glu
            500                 505                 510

Ala Leu Lys Gln Gln Lys Arg Lys Ala Lys Ala Ser Gly Glu Arg Tyr
        515                 520                 525

His Met Glu Pro His Pro Glu His Val Cys Gly Ala Tyr Pro Tyr Ala
    530                 535                 540

Tyr Pro Pro Met Pro Ala Met Val Pro His His Ala Tyr Lys Asp Trp
545                 550                 555                 560

Ser Gln Ile Arg Tyr Pro Pro Pro Val Pro Met Glu His Pro Pro
                565                 570                 575

Pro His Pro Asn Ser Arg Leu Phe His Leu Pro Glu Tyr Thr Trp Arg
            580                 585                 590

Pro Pro Cys Ala Gly Ile Arg Asn Gln Ser Ser Gln Val Met Asp Pro
        595                 600                 605

Pro Pro Asp Arg Pro Ala Glu Pro Glu Ser Ala Asp Asn Asp Cys Asp
    610                 615                 620

Gly Pro Gln
625

<210> SEQ ID NO 4
<211> LENGTH: 574
<212> TYPE: PRT
<213> ORGANISM: Mus musculus

<400> SEQUENCE: 4

Pro Pro Thr Ser Ala Pro Ser Leu Val Ser Phe Asp Asp Leu Ala Glu
1               5                   10                  15

Leu Thr Gly Gln Asp Thr Lys Val Gln Val His Pro Ala Thr Ser Thr
                20                  25                  30

Ala Ala Thr Thr Thr Ala Thr Ala Thr Thr Gly Asn Ser Met Glu Lys
```

-continued

```
                35                  40                  45
Pro Glu Pro Ala Ser Lys Ser Pro Ser Asn Gly Ala Ser Ser Asp Phe
 50                  55                  60
Glu Val Pro Thr Glu Gln Asn Ser Pro Glu Thr Gly Ser His
 65                  70                  75                  80
Pro Thr Asn Met Met Asp Leu Gly Pro Pro Pro Glu Asp Ser Asn
                 85                  90                  95
Leu Lys Leu His Leu Gln Arg Leu Glu Thr Thr Leu Ser Val Cys Ala
                100                 105                 110
Glu Glu Pro Asp His Ser Gln Leu Phe Thr His Leu Gly Arg Met Ala
                115                 120                 125
Leu Glu Phe Asn Arg Leu Ala Ser Lys Val His Lys Asn Glu Gln Arg
    130                 135                 140
Thr Ser Ile Leu Gln Thr Leu Cys Glu Gln Leu Arg Gln Glu Asn Glu
145                 150                 155                 160
Ala Leu Lys Ala Lys Leu Asp Lys Gly Leu Glu Gln Arg Asp Leu Ala
                165                 170                 175
Ala Glu Arg Leu Arg Glu Glu Asn Thr Glu Leu Lys Lys Leu Leu Met
                180                 185                 190
Asn Ser Ser Cys Lys Glu Gly Leu Cys Gly Gln Pro Ser Ser Pro Lys
                195                 200                 205
Pro Glu Gly Ala Gly Lys Lys Gly Val Ala Gly Gln Gln Ala Ser
    210                 215                 220
Val Met Ala Ser Lys Val Pro Glu Ala Gly Ala Phe Gly Ala Ala Glu
225                 230                 235                 240
Lys Lys Val Lys Leu Leu Glu Gln Gln Arg Met Glu Leu Leu Glu Val
                245                 250                 255
Asn Lys Gln Trp Asp Gln His Phe Arg Ser Met Lys Gln Gln Tyr Glu
                260                 265                 270
Gln Lys Ile Thr Glu Leu Arg Gln Lys Leu Val Asp Leu Gln Lys Gln
                275                 280                 285
Val Thr Glu Leu Glu Ala Glu Arg Glu Gln Lys Gln Arg Asp Phe Asp
    290                 295                 300
Arg Lys Leu Leu Leu Ala Lys Ser Lys Ile Glu Met Glu Glu Thr Asp
305                 310                 315                 320
Lys Glu Gln Leu Thr Ala Glu Ala Lys Glu Leu Arg Gln Lys Val Arg
                325                 330                 335
Tyr Leu Gln Asp Gln Leu Ser Pro Leu Thr Arg Gln Arg Glu Tyr Gln
                340                 345                 350
Glu Lys Glu Ile Gln Arg Leu Asn Lys Ala Leu Glu Glu Ala Leu Ser
                355                 360                 365
Ile Gln Ala Ser Pro Ser Ser Pro Ala Ala Phe Gly Ser Pro Glu
    370                 375                 380
Gly Val Gly Gly His Leu Arg Lys Gln Glu Leu Val Thr Gln Asn Glu
385                 390                 395                 400
Leu Leu Lys Gln Gln Val Lys Ile Phe Glu Glu Asp Phe Gln Arg Glu
                405                 410                 415
Arg Ser Asp Arg Glu Arg Met Asn Glu Glu Lys Glu Glu Leu Lys Lys
                420                 425                 430
Gln Val Glu Lys Leu Gln Ala Gln Val Thr Leu Thr Asn Ala Gln Leu
                435                 440                 445
Lys Thr Leu Lys Glu Glu Glu Lys Ala Lys Glu Ala Leu Lys Gln Gln
    450                 455                 460
```

-continued

```
Lys Arg Lys Ala Lys Ala Ser Gly Glu Arg Tyr His Met Glu Pro His
465                 470                 475                 480

Pro Glu His Val Cys Gly Ala Tyr Pro Tyr Ala Tyr Pro Pro Met Pro
                485                 490                 495

Ala Met Val Pro His His Ala Tyr Lys Asp Trp Ser Gln Ile Arg Tyr
            500                 505                 510

Pro Pro Pro Pro Val Pro Met Glu His Pro Pro His Pro Asn Ser
        515                 520                 525

Arg Leu Phe His Leu Pro Glu Tyr Thr Trp Arg Pro Pro Cys Ala Gly
        530                 535                 540

Ile Arg Asn Gln Ser Ser Gln Val Met Asp Pro Pro Asp Arg Pro
545                 550                 555                 560

Ala Glu Pro Glu Ser Ala Asp Asn Asp Cys Asp Gly Pro Gln
                565                 570

<210> SEQ ID NO 5
<211> LENGTH: 1967
<212> TYPE: DNA
<213> ORGANISM: Mus musculus
<220> FEATURE:
<221> NAME/KEY: CDS
<222> LOCATION: (83)...(1375)

<400> SEQUENCE: 5
aaactttccg ggaaggctgg ttttcgctcc ccctgtgtgg agaagttgga gacgcccaag      60
tccccacgga aggcctacag cc atg tcg tct ggg gac cca agg tct ggt aga     112
                        Met Ser Ser Gly Asp Pro Arg Ser Gly Arg
                         1               5                  10 cag gac ggg gcc ccg cgt gcg gcc gca gcg ctc tgt ggc ctg tac cac      160
Gln Asp Gly Ala Pro Arg Ala Ala Ala Ala Leu Cys Gly Leu Tyr His
                15                  20                  25 gag gcc ggc cag caa cta cag cgc ctg aag gat cag ctg gcc gcg cgt      208
Glu Ala Gly Gln Gln Leu Gln Arg Leu Lys Asp Gln Leu Ala Ala Arg
            30                  35                  40 gac gcc ctc atc gcg agc ctc cgc acc cgc ctc gcg gct ctg gaa ggg      256
Asp Ala Leu Ile Ala Ser Leu Arg Thr Arg Leu Ala Ala Leu Glu Gly
        45                  50                  55 cac acg gcg ccg tca ctc gtg gac gca ctt ctg gat cag gtg gag cgc      304
His Thr Ala Pro Ser Leu Val Asp Ala Leu Leu Asp Gln Val Glu Arg
    60                  65                  70 ttc cgt gag cag ctg cga cga cag gag gaa ggc gct tcg gag acc cag      352
Phe Arg Glu Gln Leu Arg Arg Gln Glu Glu Gly Ala Ser Glu Thr Gln
75                  80                  85                  90 ctg cgg cag gaa gtt gaa aga ctt acg gag cgt cta gag gaa aaa gag      400
Leu Arg Gln Glu Val Glu Arg Leu Thr Glu Arg Leu Glu Glu Lys Glu
                95                 100                 105 agg gag atg caa cag ctg atg agc cag cct cag cat gag caa gag aag      448
Arg Glu Met Gln Gln Leu Met Ser Gln Pro Gln His Glu Gln Glu Lys
            110                 115                 120 gag gta gtc ttg ctt cgg cga agt gtg gca gag aag gag aaa gcc agg      496
Glu Val Val Leu Leu Arg Arg Ser Val Ala Glu Lys Glu Lys Ala Arg
        125                 130                 135 gcc gcc agt gat gtt ctg tgc cgc tcc ttg gct gat gag acc cac caa      544
Ala Ala Ser Asp Val Leu Cys Arg Ser Leu Ala Asp Glu Thr His Gln
    140                 145                 150 ctg cgc agg aca ttg gca gcc act gcc cac atg tgc caa cat ctg gcc      592
Leu Arg Arg Thr Leu Ala Ala Thr Ala His Met Cys Gln His Leu Ala
155                 160                 165                 170
```

```
aaa tgt ctg gat gaa cga cag tgt gca cag gga gac gct ggg gag aaa      640
Lys Cys Leu Asp Glu Arg Gln Cys Ala Gln Gly Asp Ala Gly Glu Lys
                175                 180                 185 agc cct gct gag cta gag caa aca agc agc gat gct tct ggc cag agt      688
Ser Pro Ala Glu Leu Glu Gln Thr Ser Ser Asp Ala Ser Gly Gln Ser
            190                 195                 200 gtt att aag aag tta cag gaa gaa aat cga ctg tta aaa cag aag gtg      736
Val Ile Lys Lys Leu Gln Glu Glu Asn Arg Leu Leu Lys Gln Lys Val
        205                 210                 215 act cat gta gaa gac ctc aat gct aag tgg cag cgt tat gat gca agt      784
Thr His Val Glu Asp Leu Asn Ala Lys Trp Gln Arg Tyr Asp Ala Ser
    220                 225                 230 agg gac gaa tat gtg aag ggg ttg cat gcc cag cta aag agg cgg cag      832
Arg Asp Glu Tyr Val Lys Gly Leu His Ala Gln Leu Lys Arg Arg Gln
235                 240                 245                 250 gtc cct ctg gag cct gag ctg atg aag aag gag att tcc cga ctt aac      880
Val Pro Leu Glu Pro Glu Leu Met Lys Lys Glu Ile Ser Arg Leu Asn
                255                 260                 265 aga cag ttg gag gag aaa ata agt gac tgt gcg gaa gca aac cag gag      928
Arg Gln Leu Glu Glu Lys Ile Ser Asp Cys Ala Glu Ala Asn Gln Glu
            270                 275                 280 ctg aca gcc atg agg atg tcc cgg gac act gcg ctg gag cga gtg cag      976
Leu Thr Ala Met Arg Met Ser Arg Asp Thr Ala Leu Glu Arg Val Gln
        285                 290                 295 atg cta gaa cag cag att ctt gct tac aag gat gac ttc aaa tca gaa     1024
Met Leu Glu Gln Gln Ile Leu Ala Tyr Lys Asp Asp Phe Lys Ser Glu
    300                 305                 310 agg gca gat cgg gaa cga gcg cac agt agg att caa gag ctg gag gaa     1072
Arg Ala Asp Arg Glu Arg Ala His Ser Arg Ile Gln Glu Leu Glu Glu
315                 320                 325                 330 aag atc atg tcc ttg atg tac caa gtg tcc cag aga cag gac tcc cgg     1120
Lys Ile Met Ser Leu Met Tyr Gln Val Ser Gln Arg Gln Asp Ser Arg
                335                 340                 345 gag cca gga ccc tgt cgg att cat acg ggg aac aaa act gcc aag tac     1168
Glu Pro Gly Pro Cys Arg Ile His Thr Gly Asn Lys Thr Ala Lys Tyr
            350                 355                 360 tta gag atg gat gca ctg gag cat gtg acc cct ggc ggc tgg agg cct     1216
Leu Glu Met Asp Ala Leu Glu His Val Thr Pro Gly Gly Trp Arg Pro
        365                 370                 375 gag tct agg tcc caa cag atg gaa cct tct gca gag ggt ggg cat gtg     1264
Glu Ser Arg Ser Gln Gln Met Glu Pro Ser Ala Glu Gly Gly His Val
    380                 385                 390 tgc aca gcc cag aga ggt cag ggt gac ctt cag tgc cct cat tgc ctg     1312
Cys Thr Ala Gln Arg Gly Gln Gly Asp Leu Gln Cys Pro His Cys Leu
395                 400                 405                 410 cgg tgc ttc agt gat gag caa ggc gag gca ttc ctc agg cac ctg tct     1360
Arg Cys Phe Ser Asp Glu Gln Gly Glu Ala Phe Leu Arg His Leu Ser
                415                 420                 425 gag tgc tgc caa tga gccagacatt gcccgtgtga cccatgacca ccatagctgc     1415
Glu Cys Cys Gln
            430 tctaagggac tgggaggggt cctcagactc agttttcaac tcagtgtgtt gcattctcct    1475 gggatctagg gcccaaatgg gcagggtcac tggaaggtca tcttgttttc atttgaccat    1535 ggtgagactt ggtcagaggg aactattgac agagcaggag gaagagggtg gggtcaggga    1595 catcaagtgg acatcagttt tgtctcacgt agagtttgga gtgagctgtc aattcaaagc    1655 tgcaagctat cagttgtggg aatattctga agcctgcttg cacctagagt tatgccactt    1715 gctggaaggg gaagttgctg tgggagcagt gtgtcctctt tctagggtgg tagctccatc    1775
```

-continued

```
ctgttgagta gtgagataca ctccctgact ggtctgtgct gcattacagt tacatgatac    1835
actagaacct tcccaaactc agcagagcca cacagctgca tccagtacca tcaccctgca    1895
aaacacttgt atttccaaaa gggaaagcac ctttatttcc taatcattta tttttataat    1955
aaatggcttt ac                                                        1967
```

<210> SEQ ID NO 6
<211> LENGTH: 430
<212> TYPE: PRT
<213> ORGANISM: Mus musculus

<400> SEQUENCE: 6

```
Met Ser Ser Gly Asp Pro Arg Ser Gly Arg Gln Asp Gly Ala Pro Arg
1               5                   10                  15

Ala Ala Ala Ala Leu Cys Gly Leu Tyr His Glu Ala Gly Gln Gln Leu
            20                  25                  30

Gln Arg Leu Lys Asp Gln Leu Ala Ala Arg Asp Ala Leu Ile Ala Ser
        35                  40                  45

Leu Arg Thr Arg Leu Ala Ala Leu Glu Gly His Thr Ala Pro Ser Leu
    50                  55                  60

Val Asp Ala Leu Leu Asp Gln Val Glu Arg Phe Arg Glu Gln Leu Arg
65                  70                  75                  80

Arg Gln Glu Glu Gly Ala Ser Glu Thr Gln Leu Arg Gln Glu Val Glu
                85                  90                  95

Arg Leu Thr Glu Arg Leu Glu Glu Lys Glu Arg Glu Met Gln Gln Leu
            100                 105                 110

Met Ser Gln Pro Gln His Glu Gln Glu Lys Glu Val Val Leu Leu Arg
        115                 120                 125

Arg Ser Val Ala Glu Lys Glu Lys Ala Arg Ala Ala Ser Asp Val Leu
    130                 135                 140

Cys Arg Ser Leu Ala Asp Glu Thr His Gln Leu Arg Arg Thr Leu Ala
145                 150                 155                 160

Ala Thr Ala His Met Cys Gln His Leu Ala Lys Cys Leu Asp Glu Arg
                165                 170                 175

Gln Cys Ala Gln Gly Asp Ala Gly Glu Lys Ser Pro Ala Glu Leu Glu
            180                 185                 190

Gln Thr Ser Ser Asp Ala Ser Gly Gln Ser Val Ile Lys Lys Leu Gln
        195                 200                 205

Glu Glu Asn Arg Leu Leu Lys Gln Lys Val Thr His Val Glu Asp Leu
    210                 215                 220

Asn Ala Lys Trp Gln Arg Tyr Asp Ala Ser Arg Asp Glu Tyr Val Lys
225                 230                 235                 240

Gly Leu His Ala Gln Leu Lys Arg Arg Gln Val Pro Leu Glu Pro Glu
                245                 250                 255

Leu Met Lys Lys Glu Ile Ser Arg Leu Asn Arg Gln Leu Glu Glu Lys
            260                 265                 270

Ile Ser Asp Cys Ala Glu Ala Asn Gln Glu Leu Thr Ala Met Arg Met
        275                 280                 285

Ser Arg Asp Thr Ala Leu Glu Arg Val Gln Met Leu Glu Gln Gln Ile
    290                 295                 300

Leu Ala Tyr Lys Asp Asp Phe Lys Ser Glu Arg Ala Asp Arg Glu Arg
305                 310                 315                 320

Ala His Ser Arg Ile Gln Glu Leu Glu Glu Lys Ile Met Ser Leu Met
                325                 330                 335
```

```
Tyr Gln Val Ser Gln Arg Gln Asp Ser Arg Glu Pro Gly Pro Cys Arg
                340                 345                 350

Ile His Thr Gly Asn Lys Thr Ala Lys Tyr Leu Glu Met Asp Ala Leu
            355                 360                 365

Glu His Val Thr Pro Gly Gly Trp Arg Pro Glu Ser Arg Ser Gln Gln
        370                 375                 380

Met Glu Pro Ser Ala Glu Gly Gly His Val Cys Thr Ala Gln Arg Gly
385                 390                 395                 400

Gln Gly Asp Leu Gln Cys Pro His Cys Leu Arg Cys Phe Ser Asp Glu
                405                 410                 415

Gln Gly Glu Ala Phe Leu Arg His Leu Ser Glu Cys Cys Gln
                420                 425                 430

<210> SEQ ID NO 7
<211> LENGTH: 410
<212> TYPE: PRT
<213> ORGANISM: Mus musculus

<400> SEQUENCE: 7

Leu Cys Gly Leu Tyr His Glu Ala Gly Gln Gln Leu Gln Arg Leu Lys
1               5                   10                  15

Asp Gln Leu Ala Ala Arg Asp Ala Leu Ile Ala Ser Leu Arg Thr Arg
            20                  25                  30

Leu Ala Ala Leu Glu Gly His Thr Ala Pro Ser Leu Val Asp Ala Leu
        35                  40                  45

Leu Asp Gln Val Glu Arg Phe Arg Glu Gln Leu Arg Arg Gln Glu Glu
    50                  55                  60

Gly Ala Ser Glu Thr Gln Leu Arg Gln Glu Val Glu Arg Leu Thr Glu
65                  70                  75                  80

Arg Leu Glu Glu Lys Glu Arg Glu Met Gln Gln Leu Met Ser Gln Pro
                85                  90                  95

Gln His Glu Gln Glu Lys Glu Val Val Leu Arg Arg Ser Val Ala
            100                 105                 110

Glu Lys Glu Lys Ala Arg Ala Ala Ser Asp Val Leu Cys Arg Ser Leu
        115                 120                 125

Ala Asp Glu Thr His Gln Leu Arg Arg Thr Leu Ala Ala Thr Ala His
    130                 135                 140

Met Cys Gln His Leu Ala Lys Cys Leu Asp Glu Arg Gln Cys Ala Gln
145                 150                 155                 160

Gly Asp Ala Gly Glu Lys Ser Pro Ala Glu Leu Gln Thr Ser Ser
                165                 170                 175

Asp Ala Ser Gly Gln Ser Val Ile Lys Lys Leu Gln Glu Glu Asn Arg
            180                 185                 190

Leu Leu Lys Gln Lys Val Thr His Val Glu Asp Leu Asn Ala Lys Trp
        195                 200                 205

Gln Arg Tyr Asp Ala Ser Arg Asp Glu Tyr Val Lys Gly Leu His Ala
    210                 215                 220

Gln Leu Lys Arg Arg Gln Val Pro Leu Glu Pro Glu Leu Met Lys Lys
225                 230                 235                 240

Glu Ile Ser Arg Leu Asn Arg Gln Leu Glu Glu Lys Ile Ser Asp Cys
                245                 250                 255

Ala Glu Ala Asn Gln Glu Leu Thr Ala Met Arg Met Ser Arg Asp Thr
            260                 265                 270

Ala Leu Glu Arg Val Gln Met Leu Glu Gln Gln Ile Leu Ala Tyr Lys
```

-continued

```
               275                 280                 285

Asp Asp Phe Lys Ser Glu Arg Ala Asp Arg Glu Arg Ala His Ser Arg
    290                 295                 300

Ile Gln Glu Leu Glu Glu Lys Ile Met Ser Leu Met Tyr Gln Val Ser
305                 310                 315                 320

Gln Arg Gln Asp Ser Arg Glu Pro Gly Pro Cys Arg Ile His Thr Gly
                325                 330                 335

Asn Lys Thr Ala Lys Tyr Leu Glu Met Asp Ala Leu Glu His Val Thr
            340                 345                 350

Pro Gly Gly Trp Arg Pro Glu Ser Arg Ser Gln Gln Met Glu Pro Ser
        355                 360                 365

Ala Glu Gly Gly His Val Cys Thr Ala Gln Arg Gly Gln Gly Asp Leu
    370                 375                 380

Gln Cys Pro His Cys Leu Arg Cys Phe Ser Asp Gln Gly Glu Ala
385                 390                 395                 400

Phe Leu Arg His Leu Ser Glu Cys Cys Gln
                405                 410

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: consensus
      amino acid sequence 1
<220> FEATURE:
<221> NAME/KEY: misc_feature
<222> LOCATION: (1)..(19)
<223> OTHER INFORMATION: Xaa can be any amino acid

<400> SEQUENCE: 8

Glu Xaa Xaa Xaa Lys Glu Ile Xaa Arg Leu Asn Xaa Xaa Leu Glu Glu
1               5                   10                  15

Xaa Xaa Ser

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: consensus
      amino acid sequence 2
<220> FEATURE:
<221> NAME/KEY: misc_feature
<222> LOCATION: (1)..(21)
<223> OTHER INFORMATION: Xaa can be any amino acid

<400> SEQUENCE: 9

Leu Xaa Gln Gln Xaa Xaa Xaa Xaa Xaa Asp Phe Xaa Xaa Glu Arg
1               5                   10                  15

Xaa Asp Arg Glu Arg
            20

<210> SEQ ID NO 10
<211> LENGTH: 228
<212> TYPE: PRT
<213> ORGANISM: Mus musculus

<400> SEQUENCE: 10

Arg Gln Arg Glu Tyr Gln Glu Lys Glu Ile Gln Arg Leu Asn Lys Ala
1               5                   10                  15

Leu Glu Glu Ala Leu Ser Ile Gln Ala Ser Pro Ser Ser Pro Pro Ala
```

-continued

```
              20                  25                  30
Ala Phe Gly Ser Pro Glu Gly Val Gly His Leu Arg Lys Gln Glu
         35                  40                  45

Leu Val Thr Gln Asn Glu Leu Leu Lys Gln Gln Val Lys Ile Phe Glu
 50                  55                  60

Glu Asp Phe Gln Arg Glu Arg Ser Asp Arg Glu Arg Met Asn Glu Glu
65                  70                  75                  80

Lys Glu Glu Leu Lys Lys Gln Val Glu Lys Leu Gln Ala Gln Val Thr
                 85                  90                  95

Leu Thr Asn Ala Gln Leu Lys Thr Leu Lys Glu Glu Lys Ala Lys
             100                 105                 110

Glu Ala Leu Lys Gln Gln Lys Arg Lys Ala Lys Ala Ser Gly Glu Arg
             115                 120                 125

Tyr His Met Glu Pro His Pro Glu His Val Cys Gly Ala Tyr Pro Tyr
         130                 135                 140

Ala Tyr Pro Pro Met Pro Ala Met Val Pro His Ala Tyr Lys Asp
145                 150                 155                 160

Trp Ser Gln Ile Arg Tyr Pro Pro Pro Val Pro Met Glu His Pro
                 165                 170                 175

Pro Pro His Pro Asn Ser Arg Leu Phe His Leu Pro Glu Tyr Thr Trp
             180                 185                 190

Arg Pro Pro Cys Ala Gly Ile Arg Asn Gln Ser Ser Gln Val Met Asp
         195                 200                 205

Pro Pro Pro Asp Arg Pro Ala Glu Pro Glu Ser Ala Asp Asn Asp Cys
     210                 215                 220

Asp Gly Pro Gln
225

<210> SEQ ID NO 11
<211> LENGTH: 50
<212> TYPE: DNA
<213> ORGANISM: Artificial Sequence
<220> FEATURE:
<223> OTHER INFORMATION: Primer

<400> SEQUENCE: 11
gaataccagg aggcgcagat ccagcggctc aataaagctt tggaggaggc          50

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
gttgctgaaa gaggacgtca aaatctttga agagg                          35

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
gcaggtaaaa atctttgaag agaatgccca gagggaacg                      39

<210> SEQ ID NO 14
```

-continued

```
<211> LENGTH: 62
<212> TYPE: DNA
<213> ORGANISM: Artificial Sequence
<220> FEATURE:
<223> OTHER INFORMATION: Primer

<400> SEQUENCE: 14
gcaggtaaaa atctttgaag aggacttcca gagggaacgg agtgatgcgc aacgcatgcc    60
cg                                                                  62

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: mutant
      ABIN-MUT1

<400> SEQUENCE: 15

Glu Tyr Gln Glu Ala Gln Ile Gln Arg Leu Asn Lys Ala Leu Glu Glu
1               5                   10                  15

Ala Leu Ser

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: mutant
      ABIN-MUT2

<400> SEQUENCE: 16

Leu Lys Glu Glu Val Lys Ile Phe Glu Glu Asp Phe Gln Arg Glu Arg
1               5                   10                  15

Ser Asp Arg Glu Arg
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: mutant
      ABIN-MUT3

<400> SEQUENCE: 17

Leu Lys Gln Gln Val Lys Ile Phe Glu Glu Asn Ala Gln Arg Glu Arg
1               5                   10                  15

Ser Asp Arg Glu Arg
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: mutant
      ABIN-MUT4

<400> SEQUENCE: 18

Leu Lys Gln Gln Val Lys Ile Phe Glu Glu Asp Phe Gln Arg Glu Arg
1               5                   10                  15

Ser Asp Ala Gln Arg
            20
```

<210> SEQ ID NO 19
<211> LENGTH: 594
<212> TYPE: PRT
<213> ORGANISM: Mus musculus

<400> SEQUENCE: 19

Met Glu Ala Ser Arg Leu Arg Gln Lys Ala Glu Glu Leu Val Lys Asp
1               5                   10                  15

Ser Glu Leu Ser Pro Pro Thr Ser Ala Pro Ser Leu Val Ser Phe Asp
                20                  25                  30

Asp Leu Ala Glu Leu Thr Gly Gln Asp Thr Lys Val Gln Val His Pro
            35                  40                  45

Ala Thr Ser Thr Ala Ala Thr Thr Thr Ala Thr Ala Thr Thr Gly Asn
        50                  55                  60

Ser Met Glu Lys Pro Glu Pro Ala Ser Lys Ser Pro Ser Asn Gly Ala
65                  70                  75                  80

Ser Ser Asp Phe Glu Val Val Pro Thr Glu Gln Asn Ser Pro Glu
                85                  90                  95

Thr Gly Ser His Pro Thr Asn Met Met Asp Leu Gly Pro Pro Pro
            100                 105                 110

Glu Asp Ser Asn Leu Lys Leu His Leu Gln Arg Leu Glu Thr Thr Leu
            115                 120                 125

Ser Val Cys Ala Glu Glu Pro Asp His Ser Gln Leu Phe Thr His Leu
        130                 135                 140

Gly Arg Met Ala Leu Glu Phe Asn Arg Leu Ala Ser Lys Val His Lys
145                 150                 155                 160

Asn Glu Gln Arg Thr Ser Ile Leu Gln Thr Leu Cys Glu Gln Leu Arg
                165                 170                 175

Gln Glu Asn Glu Ala Leu Lys Ala Lys Leu Asp Lys Gly Leu Glu Gln
            180                 185                 190

Arg Asp Leu Ala Ala Glu Arg Leu Arg Glu Glu Asn Thr Glu Leu Lys
        195                 200                 205

Lys Leu Leu Met Asn Ser Cys Lys Glu Gly Leu Cys Gly Gln Pro
210                 215                 220

Ser Ser Pro Lys Pro Glu Gly Ala Gly Lys Lys Gly Val Ala Gly Gln
225                 230                 235                 240

Gln Gln Ala Ser Val Met Ala Ser Lys Val Pro Glu Ala Gly Ala Phe
                245                 250                 255

Gly Ala Ala Glu Lys Lys Val Lys Leu Leu Gln Gln Arg Met Glu
            260                 265                 270

Leu Leu Glu Val Asn Lys Gln Trp Asp Gln His Phe Arg Ser Met Lys
        275                 280                 285

Gln Gln Tyr Glu Gln Lys Ile Thr Glu Leu Arg Gln Lys Leu Val Asp
    290                 295                 300

Leu Gln Lys Gln Val Thr Glu Leu Ala Glu Arg Glu Gln Lys Gln
305                 310                 315                 320

Arg Asp Phe Asp Arg Lys Leu Leu Ala Lys Ser Lys Ile Glu Met
                325                 330                 335

Glu Glu Thr Asp Lys Glu Gln Leu Thr Ala Glu Ala Lys Glu Leu Arg
            340                 345                 350

Gln Lys Val Arg Tyr Leu Gln Asp Gln Leu Ser Pro Leu Thr Arg Gln
        355                 360                 365

Arg Glu Tyr Gln Glu Lys Glu Ile Gln Arg Leu Asn Lys Ala Leu Glu
    370                 375                 380

```
Glu Ala Leu Ser Ile Gln Ala Ser Pro Ser Ser Pro Pro Ala Ala Phe
385                 390                 395                 400

Gly Ser Pro Glu Gly Val Gly Gly His Leu Arg Lys Gln Glu Leu Val
                405                 410                 415

Thr Gln Asn Glu Leu Leu Lys Gln Gln Val Lys Ile Phe Glu Glu Asp
            420                 425                 430

Phe Gln Arg Glu Arg Ser Asp Arg Glu Arg Met Asn Glu Glu Lys Glu
        435                 440                 445

Glu Leu Lys Lys Gln Val Glu Lys Leu Gln Ala Gln Val Thr Leu Thr
    450                 455                 460

Asn Ala Gln Leu Lys Thr Leu Lys Glu Glu Glu Lys Ala Lys Glu Ala
465                 470                 475                 480

Leu Lys Gln Lys Arg Lys Ala Lys Ala Ser Gly Glu Arg Tyr His
                485                 490                 495

Met Glu Pro His Pro Glu His Val Cys Gly Ala Tyr Pro Tyr Ala Tyr
            500                 505                 510

Pro Pro Met Pro Ala Met Val Pro His His Ala Tyr Lys Asp Trp Ser
        515                 520                 525

Gln Ile Arg Tyr Pro Pro Pro Val Pro Met Glu His Pro Pro Pro
    530                 535                 540

His Pro Asn Ser Arg Leu Phe His Leu Pro Glu Tyr Thr Trp Arg Pro
545                 550                 555                 560

Pro Cys Ala Gly Ile Arg Asn Gln Ser Ser Gln Val Met Asp Pro Pro
                565                 570                 575

Pro Asp Arg Pro Ala Glu Pro Glu Ser Ala Asp Asn Asp Cys Asp Gly
            580                 585                 590

Pro Gln
```

INHIBITORS OF NF-KAPPAB ACTIVATION

CROSS-REFERENCE TO RELATED APPLICATIONS

This application is a divisional of application Ser. No. 09/702,953, filed Oct. 31, 2000, now U.S. Pat. No. 6,673,897, which is a continuation of International Application No. PCT/BE99/00055, filed May 5, 1999, designating the United States of America, published in English as WO 99/57133, the contents of both of which are incorporated by this reference.

REFERENCE TO SEQUENCE LISTING

This application contains a Sequence Listing appendix and a computer readable form, both of which are hereby incorporatied by reference.

TECHNICAL FIELD

This invention relates generally to biotechnology, and more particularly to novel inhibitors of the Nuclear factor kappa B (NF-κB) activating pathway useful in the treatment of NF-κB related diseases and/or in the improvement of anti-tumor treatments. The invention also relates to nucleic acids coding for the novel inhibitors. The invention relates further to the use of polypeptides, derived from these inhibitors in the treatment of NF-κB related diseases and/or cancer. Furthermore, the invention concerns pharmaceutical preparations, comprising the novel inhibitors or the polypeptides, derived from these inhibitors and methods of screening with these compounds.

BACKGROUND

NF-κB is an ubiquitously expressed transcription factor that controls the expression of a diverse range of genes involved in inflammation, immune response, lymphoid differentiation, growth control and development. NF-κB resides in the cytoplasm as an inactive dimer consisting of p50 and p65 subunits, bound to an inhibitory protein known as IκB. The latter becomes phosphorylated and degraded in response to various environmental stimuli, such as pro-inflammatory cytokines, viruses, lipopolysaccharides, oxidants, UV light and ionizing radiation. This allows NF-κB to translocate to the nucleus where it activates genes that play a key role in the regulation of inflammatory and immune responses, including genes that encode pro-inflammatory cytokines (IL-1β, TNF, GM-CSF, IL-2, IL-6, IL-11, IL-17), chemokines (IL-8, RANTES, MIP-1α, MCP-2), enzymes that generate mediators of inflammation (NO synthetase, cyclo-oxygenase), immune receptors (IL-2 receptor) and adhesion molecules (ICAM-1, VCAM-1, E-selectin). Some of these induced proteins can in turn activate NF-κB, leading to the further amplification and perpetuation of the inflammatory response. Recently, NF-κB has been shown to have an anti-apoptotic role in certain cell types, most likely by inducing the expression of anti-apoptotic genes. This function may protect tumor cells against anti-cancer treatments and opens the possibility to use NF-κB inhibiting compounds to sensitize the tumor cells and to improve the efficiency of the anti-cancer treatment.

Because of its direct role in regulating responses to inflammatory cytokines and endotoxin, activation of NF-κB plays an important role in the development of different diseases such as (Barnes and Karin, 1997): chronic inflammatory diseases, i.e., rheumatoid arthritis, asthma and inflammatory bowel disease (Brand et al., 1996); acute diseases, i.e., septic shock (Remick, 1995); Alzheimer's disease where the β-amyloid protein activates NF-κB (Behl et al., 1997); atherosclerosis, where NF-κB may be activated by oxidized lipids (Brand et al., 1997); autoimmune diseases, i.e., such as systemic lupus erythematosis (Kaltschmidt et al., 1994); or cancer by up-regulating certain oncogenes or by preventing apoptosis (Luque et al., 1997). In addition, NF-κB is also involved in viral infection since it is activated by different viral proteins, such as occurs upon infection with rhinovirus, influenza virus, Epstein-Barr virus, HTLV, cytomegalovirus or adenovirus. Furthermore, several viruses such as HIV have NF-κB binding sites in their promoter/enhancer regions (Mosialos, 1997).

Because of the potential role of NF-κB in many of the above mentioned diseases, NF-κB and its regulators have drawn much interest as targets for the treatment of NF-κB related diseases. Glucocorticoids are effective inhibitors of NF-κB, but they have endocrine and metabolic side effects when given systematically (Barnes et al., 1993). Antioxidants may represent another class of NF-κB inhibitors, but currently available antioxidants, such as acetyl-cysteine are relatively weak and unspecific (Schreck et al., 1991). Aspirin and sodium salicylate also inhibit activation of NF-κB, but only at relatively high concentrations (Kopp and Gosh, 1994). There are some natural inhibitors of NF-κB such as glyotoxin, derived from Aspergillus, but these compounds are too toxic to be used as a drug (Pahl et al., 1996). Finally, there maybe endogenous inhibitors of NF-κB, such as IL-10, that blocks NF-κB through an effect on IκB (Wang et al., 1995). However, total inhibition of NF-κB in all cell types for prolonged periods is unwanted, because NF-κB plays a crucial role in the immune response and other defensive responses.

An important role in the induction of NF-κB by TNF and IL1 has recently been demonstrated for TNF-receptor associated factors, TRAF2 and TRAF6, which are recruited to the stimulated TNF-receptor and IL-1 receptor, respectively (Rothe et al., 1995; Cao et al., 1996). Over expression of TRAF2 or TRAF6 activates NF-κB, whereas dominant negative mutants inhibit TNF or IL-1 induced activation of NF-κB in most cell types. TRAF2 knock out studies have recently shown that TRAF2 is not absolutely required for NF-κB activation, presumably because of redundancy within the TRAF family (Yeh et al. 1997). The TRAF induced signaling pathway to NF-κB was further resolved by the identification of the TRAF-interacting protein NIK, which mediates NF-κB activation upon TNF and IL-1 stimulation by association and activation of IκB kinase-α and β (IKK) (Malinin et al, 1997; Regnier et al., 1997; DiDonato et al., 1997; Zandi et al., 1997; Woronicz et al., 1997). The latter are part of a large multi-protein NF-κB activation complex and are responsible for phosphorylation of IκB, leading to its subsequent degradation and to translocation of released, active NF-κB to the nucleus. This allows a more specific inhibition of NF-κB activation by stimuli (including TNF and IL-1) that activate TRAF pathways. Based on this principle, WO 97/37016 discloses the use of NIK and other TRAF interacting proteins for the modulation of NF-κB activity.

Another protein that can associate with TRAF2 is the zinc finger protein A20 (Song et al., 1996). The latter is encoded by an immediate early response gene induced in different cell lines upon stimulation by TNF or IL-1 (Dixit et al, 1990). Interestingly, over expression of A20 blocks both TNF and IL-1 induced NF-κB activation (Jaattela et al., 1996). However, the mechanism by which A20 blocks NF-κB activation is totally unknown. In contrast to NIK, A20 does not seem to act directly on IκB resulting in alternative pathway to modulate NF-κB activation.

De Valck et al. (1997) isolated an A20 binding protein, so-called 14-3-3, using a yeast two-hybrid assay and demonstrated that NF-κB inhibition was independent from the binding of A20 to 14-3-3.

SUMMARY OF THE INVENTION

It is shown herein that other new A20 interacting proteins unexpectedly can modulate and/or inhibit NF-κB activation.

The invention includes an isolated functional protein comprising an amino acid sequence with 70-100% homology to the amino acid sequence depicted in SEQ ID NO:2, or comprising an amino acid sequence with 70-100% homology to the amino acid sequence depicted in SEQ ID NO:19, or, in the alternative, comprising an amino acid sequence with 70-100% homology to the amino acid sequence depicted in SEQ ID NO:6.

More specifically, the functional protein comprises an amino acid sequence with 70-100% homology to the amino acids 54-647 of SEQ ID NO:2, even more specifically the functional protein comprises an amino acid sequence with 70-100% homology to the amino acids 390-647 of SEQ ID NO:2, and/or comprising an amino acid sequence with 70-100% homology to the amino acids 420-647 of SEQ ID NO:2.

Homology, in this context, means identical or similar to the referenced sequence, while known replacements/modifications of any of the amino acids provided, are included as well. A homology search in this respect can be performed with the BLAST-P (Basic Local Alignment Search Tool) program well known to a person skilled in the art. For the corresponding nucleic acid sequence homology is referred to the BLASTX and BLASTN programs known in the art.

One aspect of the invention is to offer novel modulators and/or inhibitors of TNF and/or IL-1 induced NF-κB activation pathways.

An important embodiment of the invention is a protein comprising at least the amino acids of SEQ ID NO:2.

Another embodiment of the invention is a protein comprising at least the amino acids 54-647 of SEQ ID NO:2, as represented in SEQ ID NO:19.

A further embodiment of the invention is a protein comprising at least the amino acids of SEQ ID NO:6.

A further aspect of the invention is the use of a protein comprising the amino acids 420-647 of SEQ ID NO:2 to modulate and/or inhibit the NF-κB related pathway, especially the TNF and/or IL-1 induced pathways.

In addition, the invention concerns the use of a protein, comprising the consensus sequence shown in SEQ ID NO:8 and/or SEQ ID NO:9, to modulate and/or inhibit the TNF and/or IL-1 induced, NF-κB related pathway.

Another aspect of the invention is the use of these proteins in a screening method to screen compounds that interfere with the interaction of these protein(s) with other protein components of the NF-κB related pathway.

Another embodiment of the invention is the use of the above mentioned proteins, or the use of protein components screened by the above mentioned method to sensitize tumor cells and/or improve the anti-cancer treatment.

The present invention also relates to a method for identifying and obtaining an activator or inhibitor of A20 interacting protein(s) comprising the steps of:

(a) combining a compound to be screened with a reaction mixture containing the protein of the invention and a read out system capable of interacting with the protein under suitable conditions;
(b) maintaining the reaction mixture in the presence of the compound or a sample comprising a plurality of compounds under conditions which permit interaction of the protein with the read out system;
(c) identifying or verifying a sample and compound, respectively, which leads to suppression or activation of the read out system.

The term "read out system" in context with the present invention means a DNA sequence which upon transcription and/or expression in a cell, tissue or organism provides for a scorable and/or selectable phenotype. Such read out systems are well known to those skilled in the art and comprise, for example, recombinant DNA molecules and marker genes as described above.

The term "plurality of compounds" in a method of the invention is understood as a plurality of substances which may be identical.

The compound or plurality of compounds may be comprised in, for example, samples, e.g., cell extracts from animals or microorganisms. Furthermore, the compound(s) may be known in the art but hitherto not known to be capable of suppressing or activating A20 interacting proteins. The reaction mixture may be a cell free extract or may comprise a cell or tissue culture. Suitable set ups for the method of the invention are known to the person skilled in the art and are, for example, generally described in Alberts et al., Molecular Biology of the Cell, (3rd ed. 1994). The plurality of compounds may be, for instance, added to the reaction mixture or culture medium, or may be injected into the cell.

If a sample containing a compound or a plurality of compounds is identified in the method of the invention, then it is possible to isolate the compound from the original sample identified as containing the compound capable of suppressing or activating A20 interacting proteins. Additionally, one can further subdivide the original sample, for example, if it consists of a plurality of different compounds, so as to reduce the number of different substances per sample. The method can then be repeated with the subdivisions of the original sample. Depending on the complexity of the samples, the steps described above can be performed several times, preferably until the sample identified according to the method of the invention only comprises a limited number of, or only one substance(s). Preferably, the sample comprises substances of similar chemical and/or physical properties, and most preferably the substances are identical. The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, *Nature Medicine* 1 (1995), 879-880; Hupp, *Cell* 83 (1995), 237-245; Gibbs, *Cell* 79 (1994), 193-198 and references cited supra).

The invention also relates to a DNA sequence encoding the referenced proteins or a DNA sequence encoding an immunologically active and/or functional fragment of such a protein, selected from the group consisting of:

(a) DNA sequences comprising a nucleotide sequence encoding a protein comprising the amino acid sequence as given in SEQ ID NO:2;
(b) DNA sequences comprising a nucleotide sequence as given in SEQ ID NO: 1;
(c) DNA sequences hybridizing with the complementary strand of a DNA sequence as defined in (a) or (b) and encoding an amino acid sequence which is at least 70% identical to the amino acid sequence encoded by the DNA sequence of (a) or (b);

(d) DNA sequences, the nucleotide sequence of which is degenerated as a result of the genetic code to a nucleotide sequence of a DNA sequence as defined in any one of (a) to (c); and (e) DNA sequences encoding a fragment of a protein encoded by a DNA sequence of any one of (a) to (d).

Thus, the invention consists of DNA molecules, also called nucleic acid sequences, encoded for the above mentioned proteins preferably a nucleic acid sequence, with 70-100% homology to the DNA sequence depicted in SEQ ID NO:1, and/or a nucleic acid sequence with 70-100% homology to the DNA sequence depicted in SEQ ID NO:5.

Homology in this context means that the respective nucleic acid molecules or encoded proteins are functionally and/or structurally equivalent. The nucleic acid molecules that are homologous to the nucleic acid molecules described above and that are derivatives of the nucleic acid molecules are, for example, variations of the nucleic acid molecules which represent modifications having the same biological function. In particular, the modifications encode proteins with the same or substantially the same biological function. They may be naturally occurring variations, such as sequences from other varieties or species, or mutations. These mutations may occur naturally or may be obtained by mutagenesis techniques. The allelic variations may be naturally occurring allelic variants as well as synthetically produced or genetically engineered variants.

The proteins encoded by the various derivatives and variants of the above-described nucleic acid molecules have similar common characteristics, such as biological activity, molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc.

The present invention also relates to vectors, particularly plasmids, cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, *Molecular Cloning A Laboratory Manual*, Cold Spring Harbor Laboratory (1989) N.Y.

Alternatively, the nucleic acid molecules and vectors of the invention can be reconstituted into liposomes for delivery to target cells.

In a preferred embodiment, the nucleic acid molecule present in the vector is operably linked to (a) control sequence(s) which allow the expression of the nucleic acid molecule in prokaryotic and/or eukaryotic cells.

The term "control sequence" refers to regulatory DNA sequences which are necessary to affect the expression of coding sequences to which they are ligated. The nature of such control sequences differs depending upon the host organism. In procaryotes, control sequences generally include promoter, ribosomal binding site, and terminators. In eucaryotes, control sequences generally include promoters, terminators and, in some instances, enhancers, transactivators or transcription factors. The term "control sequence" is intended to include, at a minimum, all components that are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is known to a skilled person that double-stranded nucleic acid is used.

Thus, the vector of the invention is preferably an expression vector. An "expression vector" is a construct that can be used to transform a selected host cell and provides for expression of a coding sequence in the selected host. Expression vectors can, for instance, be cloning vectors, binary vectors or integrating vectors. Expression comprises transcription of the nucleic acid molecule preferably into a translatable mRNA. Regulatory elements ensuring expression in prokaryotic and/or eukaryotic cells are well known to those skilled in the art.

The present invention furthermore relates to host cells comprising a vector as described herein or a nucleic acid molecule according to the invention wherein the nucleic acid molecule is foreign to the host cell.

By "foreign" is meant that the nucleic acid molecule is either heterologous or homologous with respect to the host cell. "Heterologous" means derived from a cell or organism with a different genomic background. "Homologous" means located in a different genomic environment than the naturally occurring counterpart of the nucleic acid molecule. Thus, if the nucleic acid molecule is homologous with respect to the host cell, it is not located in its natural location in the genome of the host cell, but it is surrounded by different genes. In this case, the nucleic acid molecule may be either under the control of its own promoter or under the control of a heterologous promoter. The vector or nucleic acid molecule, according to the invention, which is present in the host cell may either be integrated into the genome of the host cell or it may be maintained in some form extra-chromosomally. It is also possible that the nucleic acid molecule of the invention can be used to restore or create a mutant gene via homologous recombination (Paszkowski (ed.), *Homologous Recombination and Gene Silencing in Plants*, (Kluwer Academic Publishers 1994)).

The host cell can be any prokaryotic or eukaryotic cell, such as bacterial, insect, fungal, plant or animal cells. Preferred fungal cells are, for example, those of the genus Saccharomyces, in particular those of the species *S. cerevisiae*.

The invention also includes a method for preparing A20 interacting proteins which method comprises the cultivation of host cells that due to the presence of a vector or a nucleic acid molecule according to the invention, are able to express such a protein under conditions which allow expression of the protein and thus recovery of the so-produced protein from the culture.

The term "expression" means the production of a protein or nucleotide sequence in the cell. However, the term also includes expression of the protein in a cell-free system. It includes transcription into an RNA product, post-transcriptional modification and/or translation to a protein product or polypeptide from a DNA encoding that product, as well as possible post-translational modifications. Depending on the specific constructs and conditions used, the protein may be recovered from the cells, from the culture medium or from both. For the person skilled in the art, it is well known that it is not only possible to express a native protein, but also to express the protein as fusion polypeptides or to add signal sequences directing the protein to specific compartments of the host cell, for example, ensuring secretion of the peptide into the culture medium, etc. Furthermore, such a protein and fragments thereof can be chemically synthesized and/or modified according to standard methods.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term also refers to and includes post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The present invention furthermore relates to proteins encoded by the nucleic acid molecules according to the invention or produced or obtained by the methods described herein, and to functional and/or immunologically active fragments of such A20 interacting proteins. The proteins and polypeptides of the present invention are not necessarily translated from a designated nucleic acid sequence. The polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art. In this context, it is also understood that the proteins according to the invention may be further modified by conventional methods known in the art. By providing the proteins according to the present invention it is also possible to determine fragments which retain biological activity, namely the mature, processed form. This allows the construction of chimeric proteins and peptides comprising an amino sequence derived from the protein of the invention, which is crucial for its binding activity. The other functional amino acid sequences may be either physically linked by, for example, chemical means to the proteins of the invention or may be fused by recombinant DNA techniques well known in the art.

The term "functional fragment of a sequence" or "functional part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is desirable to select sequences of at least about 10, 12 or 15 amino acids, up to a maximum of about 20 or 25 amino acids.

Furthermore, folding simulations and computer redesign of structural motifs of the protein of the invention can be performed using appropriate computer programs (Olszewski, *Proteins* 25 (1996), 286-299; Hoffman, *Comput. Appl. Biosci.* 11 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the inventive protein, its receptor, its ligand or other interacting proteins by computer assistant searches for complementary peptide sequences (Fassina, *Immunomethods* 5 (1994), 114-120. Further appropriate computer systems for the design of protein and peptides are described in the prior art, for example in Berry, *Biochem. Soc. Trans.* 22 (1994),1033-1036; Wodak, *Ann. N. Y. Acad. Sci.* 501 (1987), 1-13; Pabo, *Biochemistry* 25 (1986), 5987-5991. The results obtained from the above-described computer analysis can be used for, e.g., the preparation of peptidomimetics of the protein of the invention or fragments thereof. Such pseudopeptide analogues of the natural amino acid sequence of the protein may very efficiently mimic the parent protein (Benkirane, *J. Biol. Chem.* 271 (1996), 33218-33224). For example, incorporation of easily available achiral amino acid residues into a protein of the invention or a fragment thereof results in the substitution of amide bonds by polymethylene units of an aliphatic chain, thereby providing a convenient strategy for constructing a peptidomimetic (Banerjee, *Biopolymers* 39 (1996), 769-777). Superactive peptidomimetic analogues of small peptide hormones in other systems are described in the prior art (Zhang, *Biochem. Biophys. Res. Commun.* 224 (1996), 327-331). Appropriate peptidomimetics of the protein of the present invention can also be identified by the synthesis of peptidomimetic combinatorial libraries through successive amide alkylation and testing the resulting compounds, e.g., for their binding and immunological properties. Methods for the generation and use of peptidomimetic combinatorial libraries are described in the prior art. See, e.g., Ostresh, *Methods in Enzymology* 267 (1996), 220-234; Dorner, *Bioorg. Med. Chem.* 4 (1996), 709-715.

Furthermore, a three-dimensional and/or crystallographic structure of the protein of the invention can be used for the design of peptidomimetic inhibitors of the biological activity of the protein of the invention (Rose, *Biochemistry* 35 (1996), 12933-12944; Rutenber, *Bioorg. Med. Chem.* 4 (1996), 1545-1558).

Furthermore, the present invention relates to antibodies specifically recognizing a A20 interacting protein according to the invention or parts, i.e. specific fragments or epitopes, of such a protein. The antibodies of the invention can be used to identify and isolate other A20 interacting proteins and genes in any organism. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Kohler and Milstein, *Nature* 256 (1975), 495, and Galfre, *Meth. Enzymol.* 73 (1981), 3, which comprise the fusion of mouse myeloma cells to spleen cells derived from immunized mammals. Furthermore, antibodies or fragments thereof to the aforementioned peptides can be obtained by using methods which are described, for example, in Harlow and Lane "*Antibodies, A Laboratory Manual*", CSH Press, Cold Spring Harbor, 1988. These antibodies can be used, for example, for the immunoprecipitation and immunolocalization of proteins according to the invention. Additionally, the antibodies can be used for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, *Human Antibodies Hybridomas* 7 (1996), 97-105; Malmborg, *J. Immunol. Methods* 183 (1995), 7-13). In many cases, the binding phenomena of antibodies to antigens is equivalent to other ligand/anti-ligand binding.

The invention also relates to a diagnostic composition comprising at least one of the nucleic acid molecules, vectors, proteins, antibodies or compounds described herein and, optionally, a suitable means for detection.

The diagnostic compositions may be used in methods for detecting expression of related A20 interacting proteins. This is accomplished by detecting the presence of the corresponding mRNA which comprises isolation of mRNA from a cell, contacting the mRNA obtained with a probe comprising a nucleic acid probe as described herein under hybridizing conditions, detecting the presence of mRNA hybridized to the probe, and/or detecting the expression of the protein in the cell. Further methods of detecting the presence of a protein according to the present invention comprises immunotechniques well known in the art, for example, enzyme-linked immunosorbent assays.

The invention also relates to a pharmaceutical composition comprising one or more compounds, obtained by a screening method described herein, in a biologically active amount, for the treatment of NF-κB related diseases such as respiratory disorders, particularly adult respiratory distress syndrome, allograft rejection, chronic inflammatory diseases such as rheumatoid arthritis, asthma or inflammatory bowel disease, and/or autoimmune diseases such as systemic lupus erythematosis.

In another aspect, the invention relates to a pharmaceutical composition comprising one or more of the A20 interacting proteins in a biologically active amount, for the treatment of NF-κB related diseases such as respiratory disorders, particularly adult respiratory distress syndrome, allograft rejection, chronic inflammatory diseases such as rheumatoid arthritis, asthma or inflammatory bowel disease, and/or autoimmune diseases such as systemic lupus erythematosis.

The invention also concerns a pharmaceutical composition comprising one or more of the A20 interacting proteins and/or one or more of the above mentioned compounds in a biologically active amount, for a treatment to sensitize tumor cells.

BRIEF DESCRIPTION OF THE DRAWINGS

FIG. 10 shows the co-immunoprecipitation of mutated ABIN with A20 after transient expression of these genes in 293T cells. Cells were transfected with the plasmids pCAGGS-GFP or pCAGGS-GFP/A20 together with the plasmids encoding ABIN or its site specific mutants (ABIN-MUT1, ABIN-MUT2, ABIN-MUT3 or ABIN-MUT4). Lysates of these cells were immunoprecipitated with polyclonal anti-GFP antibody and separated on SDS-PAGE. Western blot analysis was performed with monoclonal anti-E-tag antibody to look for the Co-immunoprecipitation of ABIN or its mutants (upper panel). Lower panels show total expression levels of GFP, GFP/A20 and ABIN. In this case, a fraction of the total lysate was separated by SDS-PAGE and expression was detected with anti-GFP or anti-E-tag antibodies.

FIG. 11 is a bar graph depicting the effect of mutated ABIN on TNF-induced NF-κB activation. 293T cells were transiently transfected with 100 ng pUT651, 100 ng pNFconluc and 200 ng expression plasmid as indicated and stimulated with TNF (1000 IU/ml) during 6 hours. Cell extracts were analyzed for luciferase and β-galactosidase activity and plotted as luc/gal, which is representative for NF-κB activity. Each value is the mean (N=3) with standard deviations less than 10%.

FIG. 12 is a bar graph depicting the dominant negative effect of ABIN-MUT2, ABIN-MUT3 and ABIN-MUT4 on the NF-κB inhibiting function of ABIN. 293T cells were transiently transfected with 100 ng pUT651, 100 ng pNFcon-luc and 200 ng pCAGGS-ABIN or empty vector. In addition, 600 ng of the expression vectors encoding ABIN-MUT2, ABIN-MUT3, ABIN-MUT4 or empty vector were co-transfected, as indicated. Cells were stimulated with TNF (1000 IU/ml) during 6 hours. Cell extracts were analyzed for luciferase and β-galactosidase activity and plotted as 1 uc/gal.

DETAILED DESCRIPTION OF THE INVENTION

Figure 1:
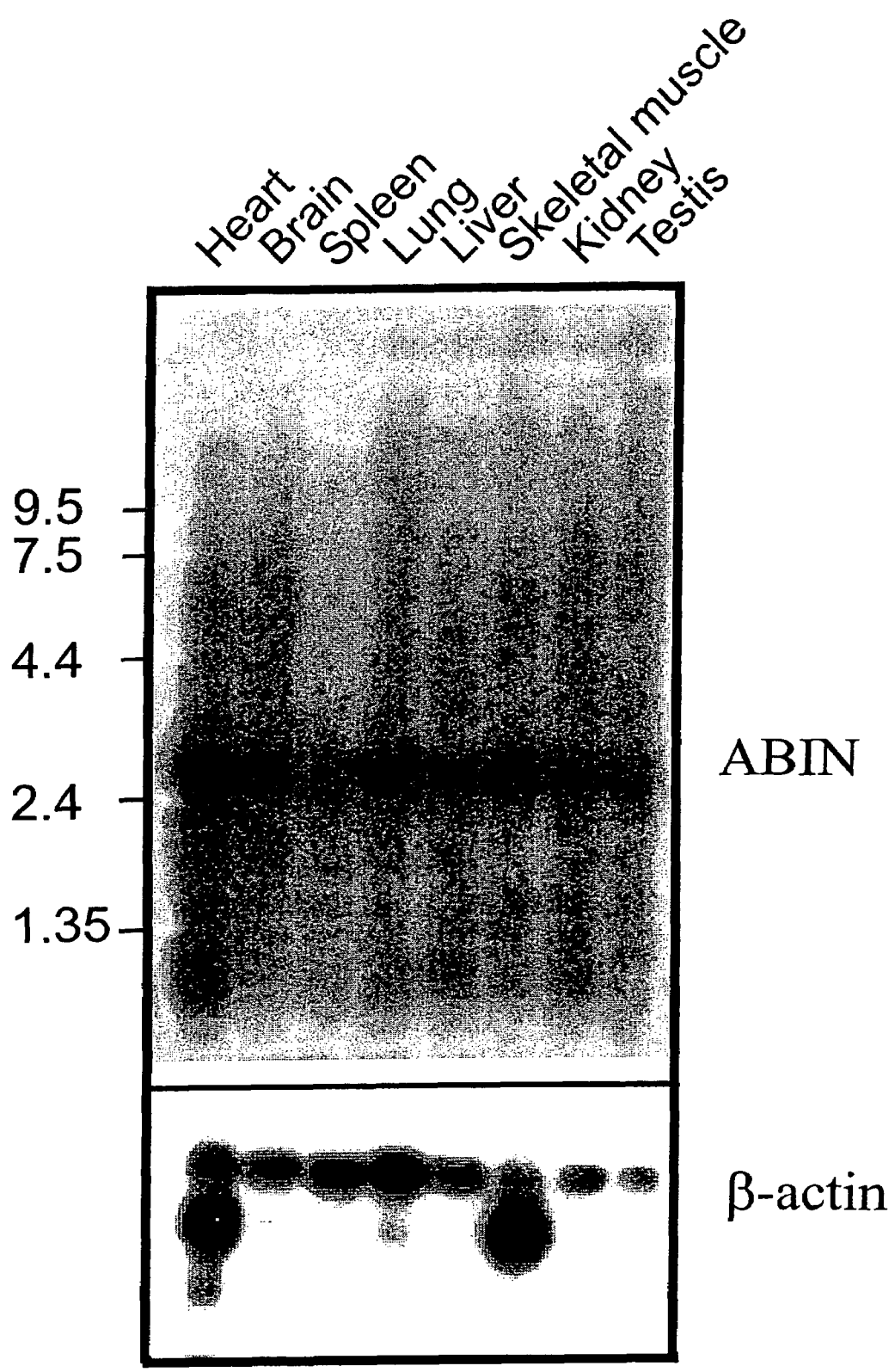
FIG. 1: Tissue distribution of ABIN transcripts. A Northern blot of poly(A)+RNA (2 μg per lane) of various murine tissues (Clontech) was probed with the fragment of ABIN cloned by two hybrid analysis covering the C-terminal sequences ABIN (390-599). RNA size markers are indicated in kB. Expression of β-actin served as a control for the quantity of RNA loaded.

The following definitions are provided in order to further illustrate and define the meaning and scope of the various terms used in the current description.

The term "treatment", "treating" or "treat" means any treatment of a disease in a mammal, including: (1) preventing the disease causing the clinical symptoms of the disease not to develop; (2) inhibiting the disease arresting the development of the clinical symptoms; and/or (3) relieving the disease causing the regression of clinical symptoms.

The term "effective amount" means a dosage sufficient to provide treatment for the disease state being treated. This will vary depending on the patient, the disease and the treatment being effected.

"Capable of interacting" means that a protein can form a complex with another protein, as can be measured using a yeast two hybrid system, or with co-immunoprecipitation, or with equivalent systems known to people skilled in the art.

"Functional" protein or fragment means a protein or fragment that is capable to interact with the zinc finger protein A20, or with another protein of the NF-κB related pathway.

"Protein A20" ("A20") means the TNF induced zinc finger protein, described by (Dixit et al., 1990; Opipari et al., 1990; Tewari et al., 1995), or an active fragment thereof, such as the zinc finger containing part (amino acids 387-790 of human A20; amino acids 369-775 of murine A20).

The terms "gene(s)", "polynucleotide", "nucleic acid sequence", "nucleotide sequence", "DNA sequence" or "nucleic acid molecule(s)" as used herein refer to a polymeric form of nucleotides of any length, either ribonucleotides or deoxyribonucleotides. These terms refer only to the primary structure of the molecule. Thus, the term includes double- and single-stranded DNA, and RNA. It also includes known types of modifications, for example, methylation, "caps" substitution of one or more of the naturally occurring nucleotides with an analog. Preferably, the DNA sequence of the invention comprises a coding sequence encoding the above defined A20 interacting protein.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

"Consensus sequence" means a stretch of at least 15 amino acids, showing 50-100% homology, preferably between 70-100% homology between ABIN and ABIN2.

"Compound" means any chemical or biological compound, including simple or complex inorganic or organic molecules, peptides, peptido-mimetics, proteins, antibodies, carbohydrates or nucleic acids, that interfere in the binding between a protein depicted in SEQ ID NOS:2, 19, 6, 8 or 9 with a compound of the NF-κB related pathway, such as A20.

As used herein, the term "composition" refers to any composition such as a pharmaceutical composition comprising an active ingredient of an isolated functional protein according to the present invention. This may be performed in the presence of suitable excipients known to the skilled man and may be administered in the form of any suitable composition as detailed below, and by any suitable method of administration within the knowledge of a skilled man. The preferred route of administration is parenterally. In parenteral administration, the compositions of this invention will be formulated in a unit dosage injectable form such as a solution, suspension or emulsion, in association with a pharmaceutically acceptable excipient. Such excipients are inherently nontoxic and non-therapeutic. Examples of such excipients are saline, Ringer's solution, dextrose solution and Hank's solution. Non-aqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The isolated functional protein of the invention is administered at a concentration that is therapeutically effective to prevent allograft rejection, GVHD, allergy and autoimmune diseases. The dosage and mode of administration will depend on the individual. Generally, the compositions are administered so that the isolated functional protein is given at a dose between 1 μg/kg and 10 mg/kg, more preferably between 10 μg/kg and 5 mg/kg, most preferably between 0.1 and 2 mg/kg. Preferably, it is given as a bolus dose. Continuous short time infusion (during 30 minutes) may also be used. The compositions comprising the isolated functional protein according to the invention may be infused at a dose between 5 and 20 μg/kg/minute, more preferably between 7 and 15 μg/kg/minute.

The "therapeutically effective amount" of the isolated functional protein needed in a specific case, according to the invention, should be determined as being the amount sufficient to cure the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

With regard to the use of the isolated functional protein of the present invention to prevent allograft rejection, it should be stressed that the proteins of the present invention or the compositions comprising the same may be administered before, during or after the organ transplantation as is desired from case to case. In case the protein or the compositions comprising the same are administered directly to the host, treatment will preferably start at the time of the transplantation and continue afterwards in order to prevent the activation and differentiation of host T cells against the MHC on the allograft. In case the donor organ is ex vivo perfused with the functional protein according to the invention or the compositions comprising the same, treatment of the donor organ ex vivo will start before the time of the transplantation of the donor organ in order to prevent the activation and differentiation of host T cells against the MHC on the allograft.

The invention is hereunder further explained by way of examples without being restrictive in the scope of the current invention.

EXAMPLES

Example 1

Isolation of the Novel Inhibitors

The novel inhibitors of the NF-κB pathway were isolated using a yeast two-hybrid assay, with protein A20 as bait. The yeast two-hybrid assay was purchased from Clontech Laboratories (Palo Alto, Calif.). The screening of an L929r2 cDNA library with pAS2-A20 was described previously (De Valck et al., 1997). Yeast colonies expressing interacting proteins were selected by growth on minimal media lacking Tryptophan, Leucine and Histidine, in the presence of 5 mM 3-amino-1, 2,4-triazole and by screening for β-gal activity. Plasmid DNA was extracted from the positive colonies and the pGAD424 vectors encoding candidate A20 interacting proteins were recovered by electroporation in the E. coli strain HB101 and growth on media lacking Leucine.

From $1.3 \times 10^6$ transformants, 11 clones expressed A20 interacting proteins, including A20 itself (De Valck et al., 1996) and 14-3-3 proteins (De Valck et al., 1997). Three clones contained C-terminal fragments of the same cDNA encoding an unknown protein that herewith is named A20 Binding Inhibitor of NF-κB activation (ABIN) and 1 clone contained the C-terminal fragment (1136 bp) of an unknown protein that herewith is called ABIN2.

Full length ABIN cDNA was subsequently isolated from the L929r2 cDNA library by colony hybridization (De Valck et al., 1996) with an ABIN fragment (corresponding to amino acids 390-599) cloned by two-hybrid analysis as a probe. Several cDNA's were isolated and in the longest cDNA stop codons were identified in all three reading frames 5' of a potential initiator methionine. Two different splice variants were found of approximately 2800 and 2600 nucleotides long, with an open reading frame of 1941 and 1781 nucleotides respectively, initiating at two different methionines (ABIN (1-647) (SEQ ID NO:2) and ABIN (54-647) (SEQ ID NO:19)). These cDNA's encode proteins of 72 and 68 kDa containing an amphipathic helix with 4 consecutive repeats of a leucine followed by 6 random amino acids residues characteristic of a leucine zipper structure.

Full length cDNA of ABIN2 was isolated from murine heart by 5' RACE (SMART PCR cDNA synthesis kit, Clontech), using a 3' primer hybridizing to an EST clone (572231) which corresponds to the ABIN2 fragment isolated by two hybrid analysis, but with 507 extra nucleotides at the 5' end. A 1,967 nucleotide long cDNA was isolated (SEQ ID NO:5), with an open reading frame of 1,290 nucleotides long, encoding a protein of 430 amino acids (SEQ ID NO:6).

Example 2

Expression Pattern of ABIN and ABIN2.

Northern blot analysis revealed that both ABIN and ABIN2 are expressed in all murine tissues tested (heart, brain, spleen, lung, liver, skeletal muscle, kidney, testis: see FIG. 1; only the data for ABIN are shown). ABIN is present as mRNA of approximately 2800 bp which is in accordance with the length of the cloned full length cDNA. In contrast to A20, ABIN mRNA is constitutively expressed in both TNF-sensitive and TNF-resistant subclones derived from the parental cell line L929s, irrespective of TNF stimulation.

ABIN2 is present as mRNA of approximately 2,000 bp, which is in accordance with the length of the cloned, full length cDNA.

Example 3

Study of the Interaction of the ABIN and ABIN2 Proteins and Protein Fragments With A20.

Full length ABIN(1-647) and ABIN(54-647) were able to bind A20 in a yeast two hybrid assay, confirming the original interaction found with the 3 C-terminal fragments ABIN (390-599), ABIN(249-647) and ABIN(312-647). The latter contain the putative leucine zipper protein interaction motif (397-420).

Further analysis was carried out by co-immunoprecipitation. The eukaryotic plasmids for ABIN and its fragments as well as for ABIN2 were made by inserting the corresponding PCR fragment in frame with an N-terminal E-tag into the mammalian expression plasmid pCAGGS (Niwa et al., 1991). cDNA encoding mutant GFP(S65T) and a fusion protein of GFP(S65T) with murine A20 were also cloned in pCAGGS.

$2 \times 10^6$ human embryonic kidney 293T cells were plated on 10-cm Petri dishes and transiently transfected with the suitable plasmids by calcium phosphate-DNA co-precipitation. 24 hours after transfection, cells were lysed in 500 µl of lysis buffer (50 mM Hepes pH 7.6, 250 mM NaCl, 0.1% Nonidet P-40 and 5 mM EDTA). Lysates were incubated with 5 µl of rabbit anti-GFP antibody (Clontech) and immunocomplexes were immobilized on protein A-trisacryl (Pierce). The latter was washed twice with lysis buffer and twice with lysis buffer containing 1 M NaCl. Co-precipitating proteins were separated by SDS-PAGE and revealed by Western blotting with mouse anti-E-tag antibody (Pharmacia).

Figure 2:
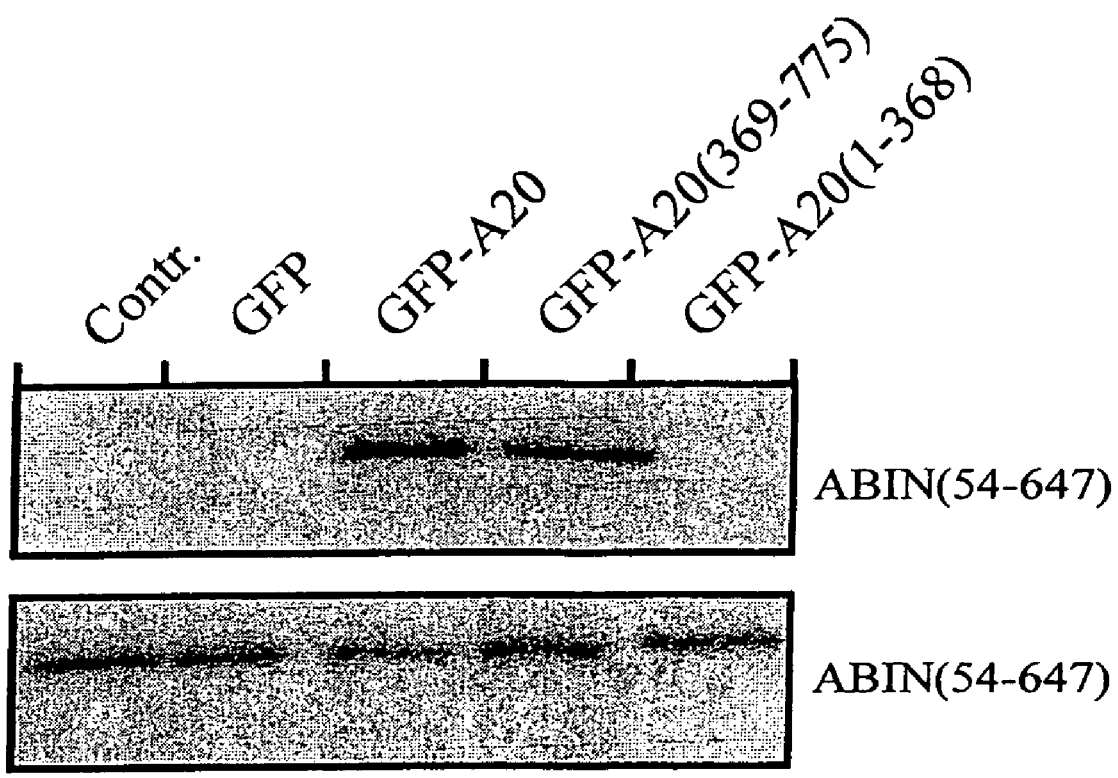
FIG. 2: Co-immunoprecipitation of A20 and ABIN after transient transfection of the encoding plasmids of E-tagged ABIN and Green Fluorescent Protein (GFP), GFP-A20, GFP-A20(369-775), GFP-A20(1-368) or an empty expression vector as a negative control in 239T cells. Immunoprecipitation (upper panel) was performed with anti-GFP antibody and Western blot detection with anti E-tag antibody. To control expression levels of ABIN, 10 μl aliquots of lysates were separated by sodium dodecyl sulphate polyacrylamide gel electrophoresis (SDS-PAGE) and Western blot detection with anti-E-tag antibody (lower panel).
Figure 3:
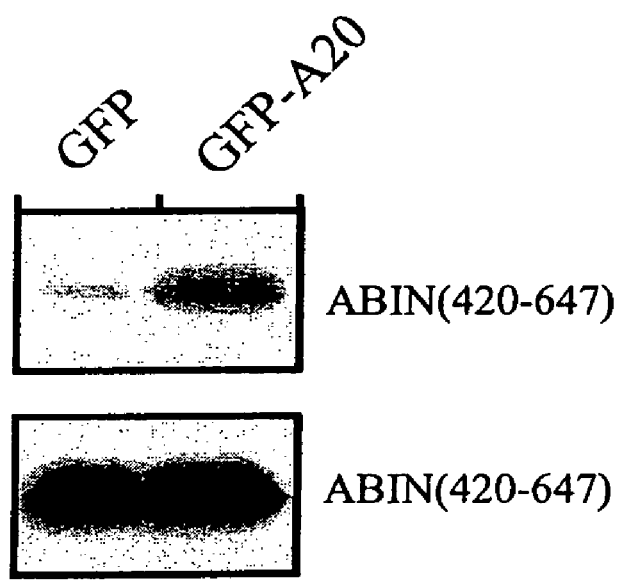
FIG. 3: Co-immunoprecipitation of the C-terminal fragment of ABIN lacking the putative leucine zipper structure with GFP-A20 upon transient over expression in 293T cells. Immunoprecipitation and expression levels were detected as described for full length ABIN and are shown in the upper and lower panel, respectively.

Full length ABIN as well as the C-terminal fragment lacking the leucine zipper motif (ABIN(420-647)) was still able to co-immunoprecipitate with A20 in 293T cells that were transiently transfected with an expression plasmid for chimeric GFP-A20 protein and full length or truncated ABIN with an N-terminal E-tag (FIG. 2). Interaction of ABIN with A20 required the C-terminal, zinc finger containing part of A20 (A20(369-775)). This domain was shown previously to be required for dimerization of A20 and for the interaction of A20 with 14-3-3 protein (De Valck et al., 1996; De Valck et al., 1997). In contrast, the N-terminal part of human A20 (A20(1-386)) was previously shown to interact with TRAF2 (Song et al., 1996), suggesting that A20 acts as an adapter protein between TRAF2 and ABIN. The interaction between A20 and ABIN was not influenced by stimulation with TNF.

To characterize the sub-cellular distribution of ABIN, we transiently transfected GFP-A20- and E-tagged ABIN cDNA in 293T cells and analyzed their expression by means of GFP fluorescence and immunofluorescence via the anti-E tag antibody. $4 \times 10^5$ 293T cells were seeded on cover slips in 6-well plates and transfected with 1 µg plasmid DNA. 24 hours after transfection, cells were fixed on the cover slips with 3% paraformaldehyde. Upon permeabilization with 1% Triton X-100, the cells were incubated for 2 hours with mouse anti-E-tag antibody (1/1000) followed by a second incubation with anti-mouse Ig antibody coupled to biotin (Amersham, 1/1000). After subsequent incubation with streptavidin coupled to Texas Red (Amersham), fluorescence can be analyzed via fluorescence microscopy (Zeiss, Axiophot) using a filter set with excitation at 543 nm and emission at 600 nm. In the same cells, fluorescence of GFP can be detected at a different wave length, namely absorption at 485 nm and emission at 510 nm.

ABIN co-localized with A20 throughout the cytoplasm, both in unstimulated and in TNF stimulated cells. This observation makes the existence of regulatory redistribution events rather unlikely.

Example 4

Sequence Analysis of the cDNA's.

Nucleotide sequence analysis was carried out using cycle sequencing on an ABI373A sequencer (Applied Biosystems, Foster City, Calif.). The sequence of full length ABIN is shown in SEQ ID NO:1; the sequence of ABIN2 is shown in SEQ ID NO:5.

Database similarity searches (BLAST) showed that ABIN is the murine homologue of the partial human cDNA encoding a protein with an unknown function (Genbank accession number D30755; Nagase et al., 1995). Moreover, ABIN shows homology with a partial human immunodeficiency virus (HIV) Nef interacting protein, NIP40-1 (no called Naf1=nef associated factor 1; Fukushi et al., FEBS Letters, 442 (1999), 83-88). HIV-Nef contributes substantially to disease pathogenesis by augmenting virus replication and markedly perturbing T-cell function. Interestingly, the effect of Nef on host cell activation has been explained in part by its interaction with specific cellular proteins involved in signal transduction (Harris, 1996) of which ABIN might be an example.

There are no proteins in the database that are clearly homologous with ABIN2. However, by comparing ABIN2 with ABIN, one can define two homologous regions and derive two consensus sequences (SEQ ID NO:8 and SEQ ID NO:9)) that may be important for the interaction of these proteins with A20, and/or for their further function in signal transduction. A consensus sequence of ABIN and ABIN2 is found from amino acids 423 to 441 and 475 to 495 of SEQ ID NO:2 for ABIN, and from amino acids 256 to 274 and 300 to 320 of SEQ ID NO:6 for ABIN2. The consensus sequence illustrates 22 amino acids from ABIN and ABIN2 that overlap with one another.

Example 5

Role of ABIN, ABIN Fragments and/or ABIN2 in the TNF-, IL-1- and/or TPA-induced Transduction Pathway Leading to NF-κB Activation, as Measured by Reporter Gene Activity.

The construction of the ABIN, ABIN-fragments and ABIN2 plasmids was carried out as described above. The plasmid pNFconluc, encoding a luciferase reporter gene driven by a minimal NF-κB responsive promoter described by Kimura et al. (1986) and the plasmid pUT651, encoding β-galactosidase was obtained from Eurogentec (Seraing, Belgium). NF-κB activity was determined by the NF-κB dependent expression of a luciferase reporter gene. Therefore, 293T cells were plated in 6-well plates at $4 \times 10^5$ cells per well and transiently transfected by the calcium phosphate-DNA coprecipitation method. Each transfection contained 800 ng of the expression plasmids, as well as 100 ng of pNFconluc plasmid as reporter and 100 ng pUT651 plasmid as a reference for transfection efficiency. 24 hours after transfection, these cells were trypsinized and seeded on a 24-well plate. Another 24 hours later, cells were either stimulated with 1000 IU/ml hTNF, 20 ng/ml mIL1-β, 200 ng/ml TPA (Sigma) or left untreated. After 6 hours of stimulation, cells were lysed in 200 µl lysis buffer and analyzed for luciferase and β-galactosidase activity as described in De Valck et al., 1997. GFP and GFP-A20 served as negative and positive controls, respectively.

Figure 4:
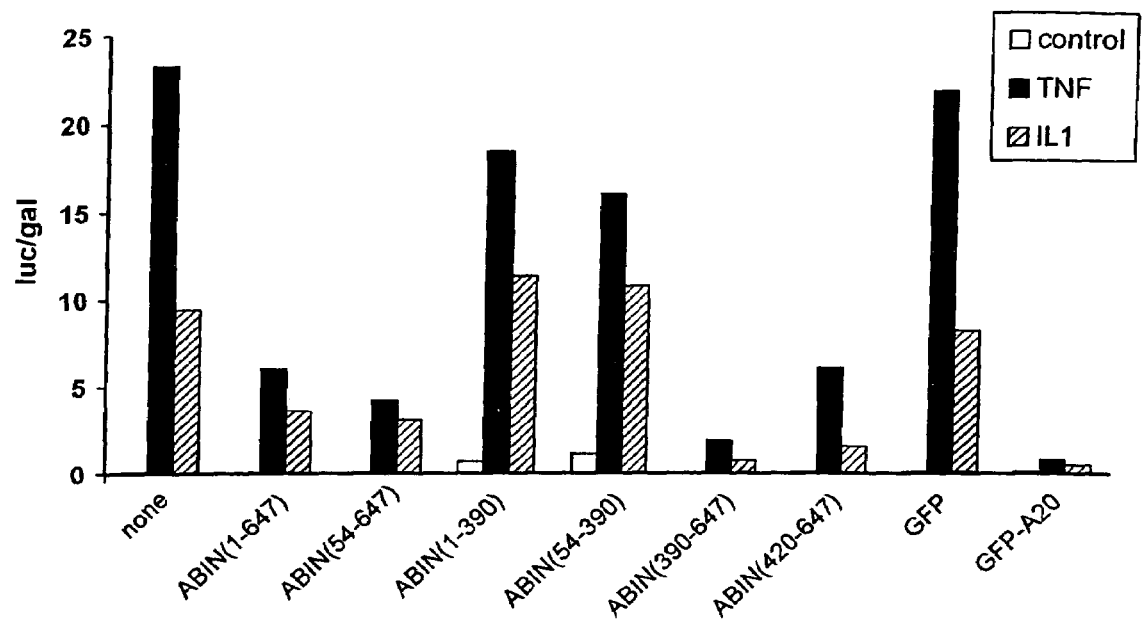
FIG. 4 is a bar graph depicting the effect of ABIN or fragments of ABIN on the TNF- and IL-1-induced activation of NF-κB, as measured by reporter gene activity. 293T cells were transiently transfected with 100 ng pUT651, 100 ng pNFconluc and 100 ng expression plasmid and stimulated with hTNF (1000 IU/ml) or mIL1β (20 ng/ml) during 6 hours. As a control, 100 ng of plasmids encoding GFP or GFP-A20 were transfected.
Figure 4:
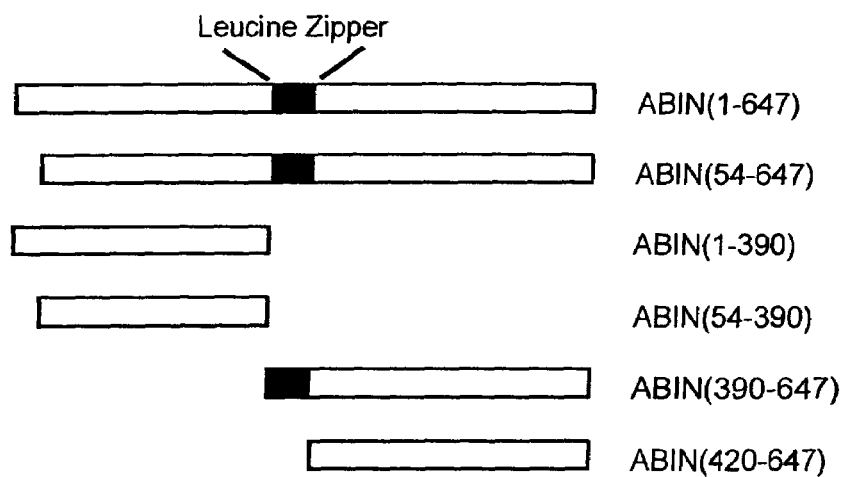
Figure 5:
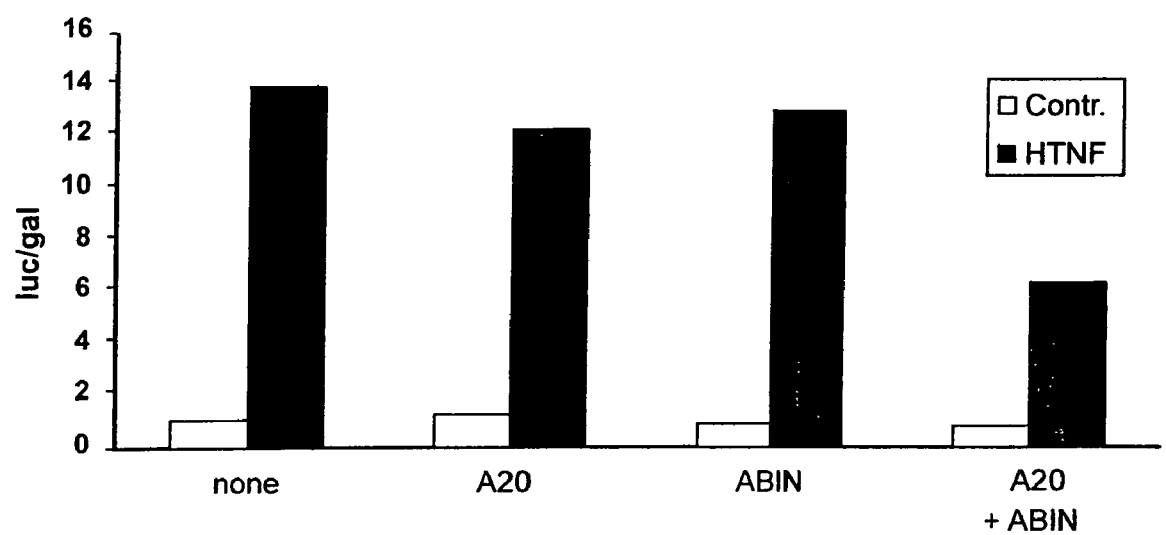
FIG. 5 is a bar graph depicting the effect of transient transfection of sub-optimal quantities of expression plasmids encoding A20 (5 ng) and ABIN (20 ng) on TNF mediated NF-κB induction in 293T cells. In both experiments, standard deviations were less than 10%.

Similar to A20, both splice variants of ABIN were able to block TNF or IL-1 induced NF-κB activation in these cells, with the shorter N-terminal truncated isoform being slightly more effective (FIG. 4). Moreover, structure-function analysis of ABIN deletion mutants revealed that the NF-κB inhibiting activity resides in the C-terminal 228 amino acids (ABIN(420-647) SEQ ID NO:10) which are also sufficient for interaction with A20. The latter ABIN-mutant no longer contains the leucine zipper structure, demonstrating that this protein domain is not involved in the interaction with A20 nor in the inhibition of NF-κB (FIG. 4). Overexpression of a combination of suboptimal doses of A20 and ABIN, that on their own were not sufficient to inhibit NF-κB activation, diminished NF-κB activation upon stimulation with TNF (FIG. 5) or IL-1 considerably. This suggests that ABIN mediates the NF-κB inhibiting effect of A20.

Figure 6:
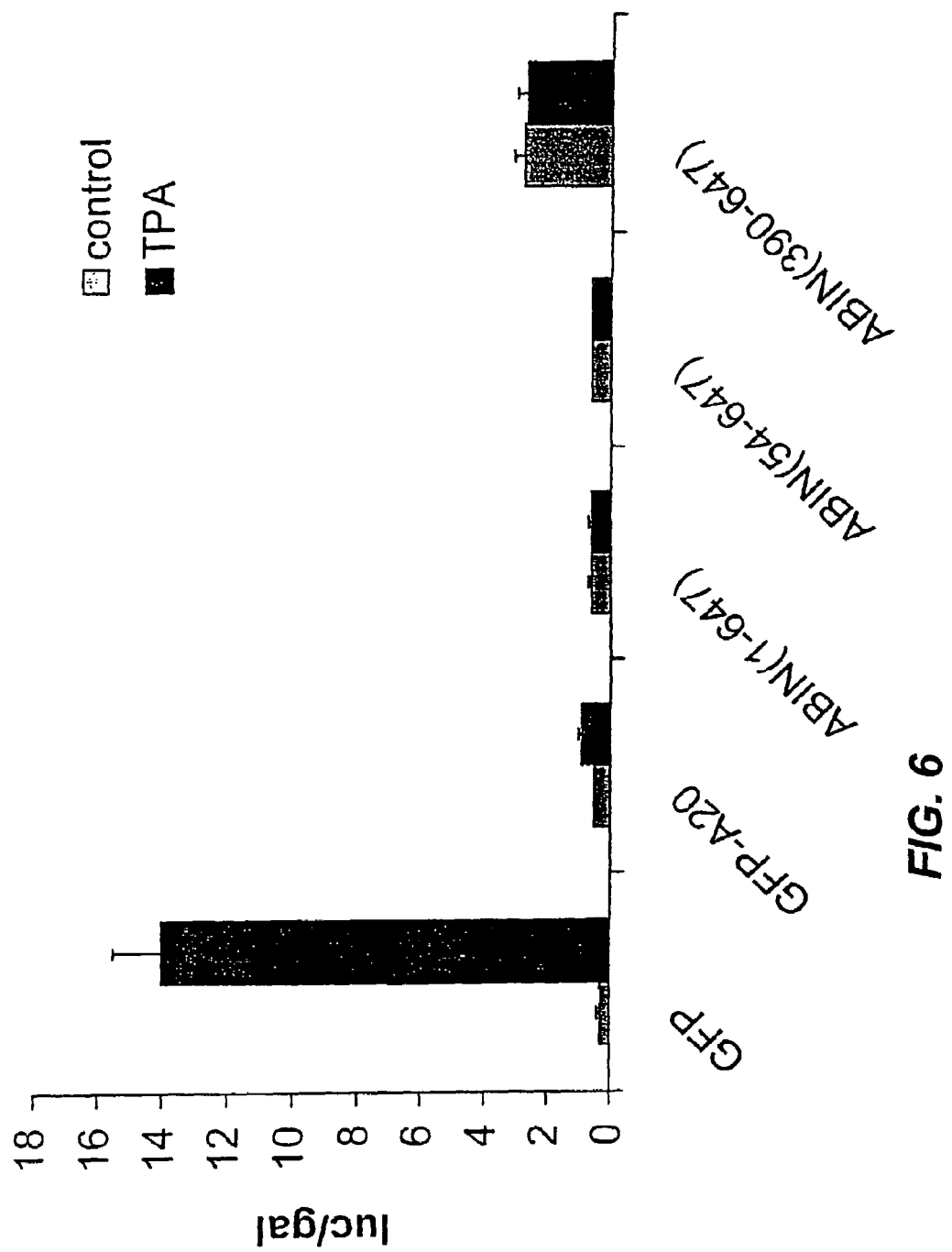
FIG. 6 is a bar graph depicting the effect of ABIN or fragments of ABIN on the TPA-induced activation of NF-κB, as measured by reporter gene activity. 293T cells were transiently transfected with 100 ng pUT651, 100 ng pNFconluc and 100 ng expression plasmid and stimulated with TPA (200 ng/ml) during 6 hours. As a control, 100 ng of plasmids encoding GFP or GFP-A20 were transfected.

Total ABIN (1-647; SEQ ID NO:2), the shorter splice variant (54-647; SEQ ID NO:19) and the C-terminal fragment (390-647) are also able to block the TPA induced NF-κB activation (FIG. 6).

Figure 7:
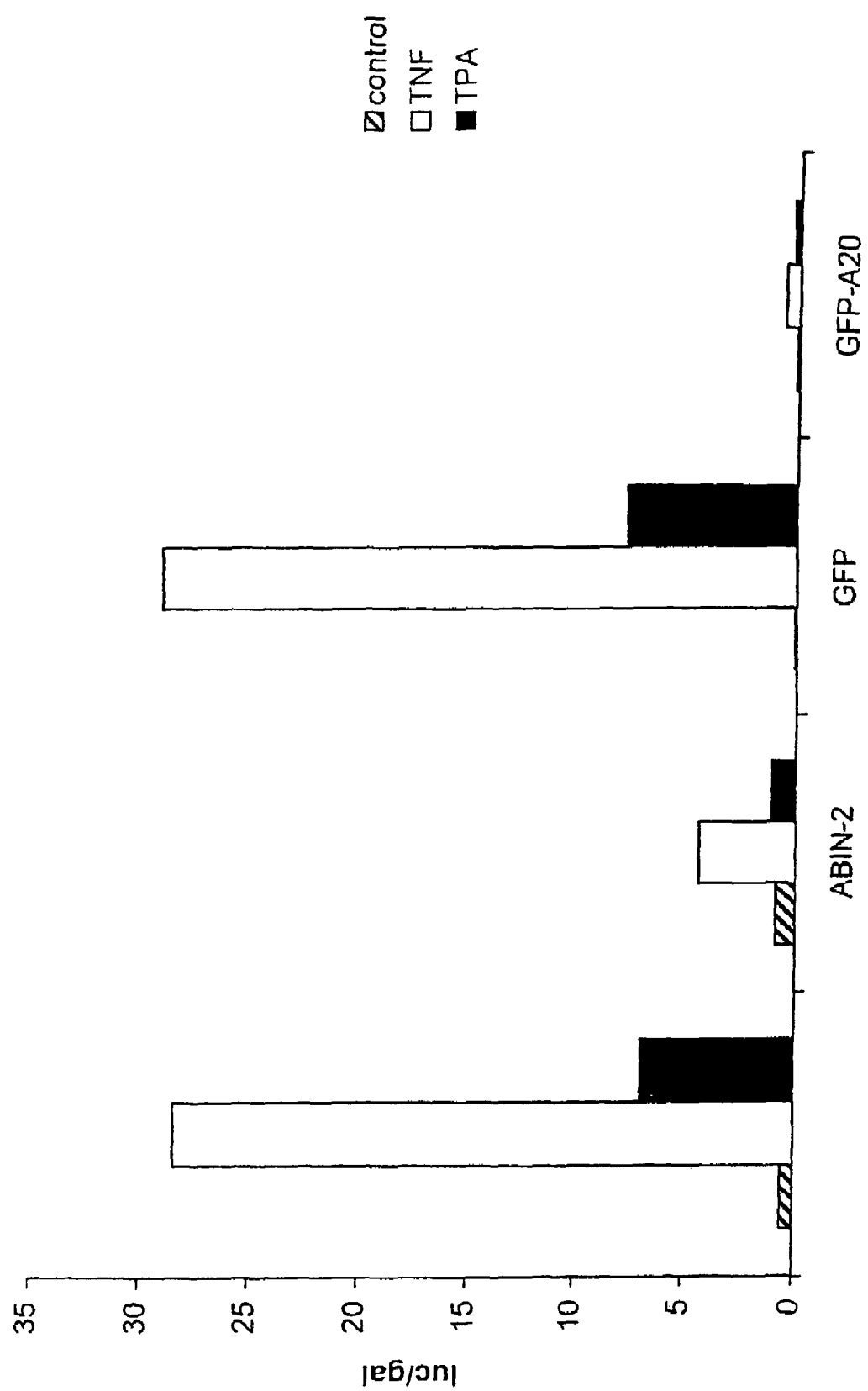
FIG. 7 is a bar graph depicting the effect of ABIN2 on the TNF- and TPA-induced activation of NF-κB, as measured by reporter gene activity. 293T cells were transiently transfected with 100 ng pUT651, 100 ng pNFconluc and 600 ng expression plasmid and stimulated with hTNF (1000 IU/ml) or TPA (200 ng/ml) during 6 hours. As a control, 600 ng of plasmid encoding GFP or GFP-A20 was transfected.

Similar results were obtained when ABIN2 was used in the test instead of ABIN or ABIN-fragments (FIG. 7).

Example 6

Effect of ABIN and/or ABIN Fragments on NF-κB Activation Induced by Overexpression of TRADD, RIP, TRAF2, NIK or p65.

Expression vectors for ABIN and ABIN fragments were constructed as described above. The expression vectors containing TRAF2, NIK and p65 have previously been described (Malinin et al., 1997; Rothe et al., 1994; Vanden Berghe et al., 1998). PCR fragments encoding TRADD and RIP were cloned in pCDNA3 (Invitrogen, Carlsbad, Calif.) in frame with a C-terminal E-tag. Transfection and reporter assay was carried out as described above.

Figure 8:
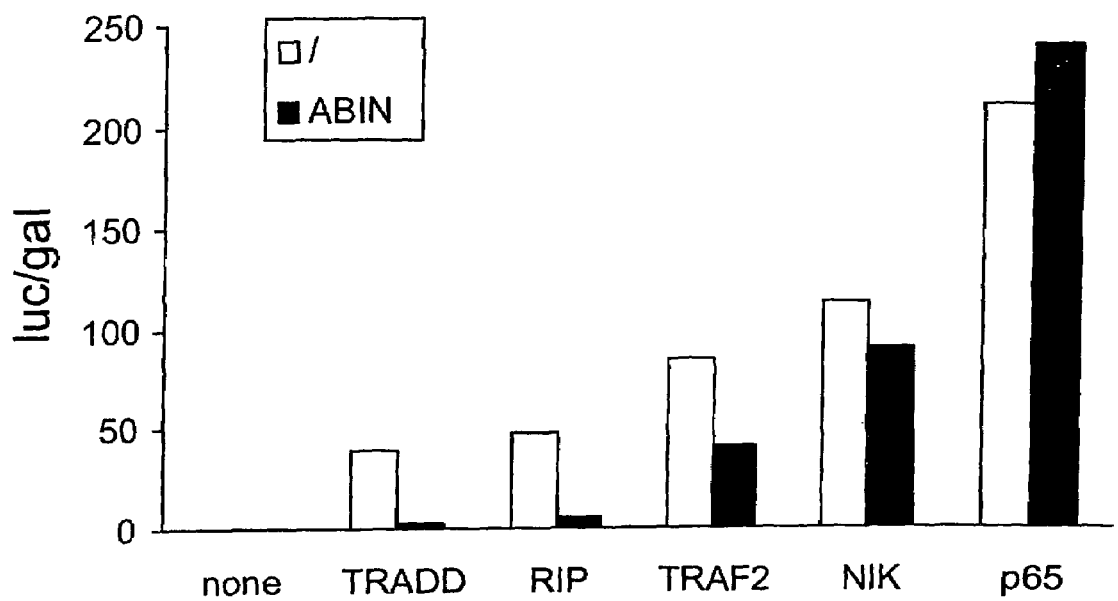
FIG. 8 is a bar graph depicting the effect of full length ABIN on NF-κB activation in 293T cells induced by over expression of TRADD, RIP, TRAF2, NIK or p65 after transfection of 300 ng of their encoding plasmids, together with 100 ng pUT651, 100 ng pNFconluc and 500 ng pCAGGS-ABIN. Cells were lysed 24 hours after transfection, and luciferase and β-galactosidase activity were measured.
Figure 9:
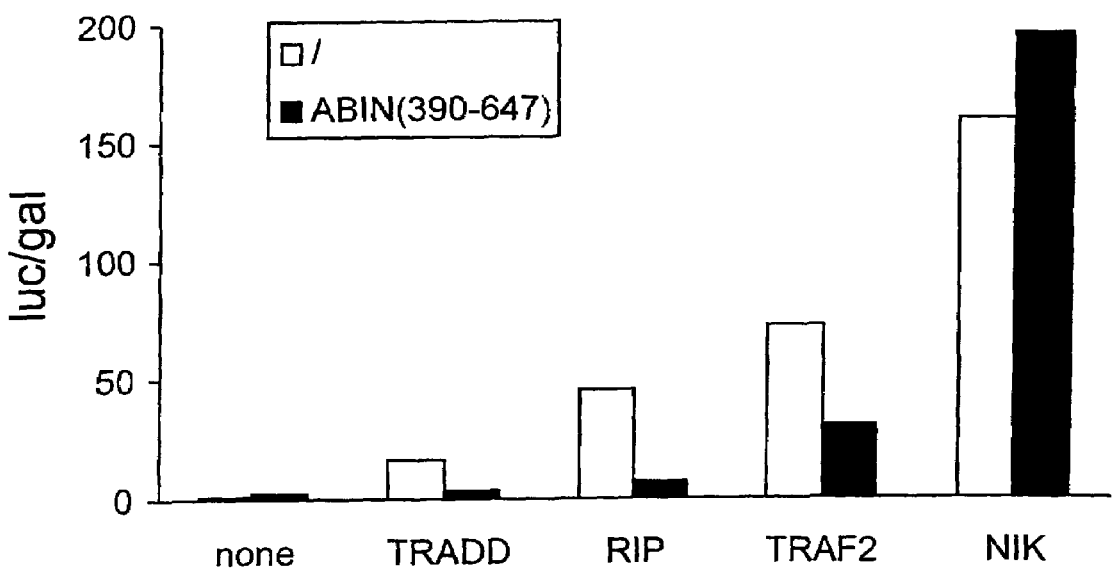
FIG. 9 specifically is a bar graph depicting the effect of truncated ABIN containing the leucine zipper structure (ABIN(390-647)) on TRADD, RIP, TRAF2 or NIK induced NF-κB activation. In both experiments, standard deviations were less than 10%.

NF-κB can be activated in 293 T cells by TNF treatment as well as by overexpression of specific proteins of the TNF-receptor complex, including TRADD, RIP, TRAF2 and NIK (Rothe et al., 1995; Malinin et al., 1997; Hsu et al., 1995; Ting et al., 1996). The latter associates with and activates IκB kinase complex which leads to IκB phosphorylation. This is a signal for ubiquitination and degradation of IκB, thus releasing NF-κB which then translocates to the nucleus. Co-transfection of expression plasmids encoding these TNF-receptor associated proteins together with the expression plasmids encoding full length ABIN, showed that the latter completely inhibited NF-κB activation induced by TRADD or RIP, and partially inhibited TRAF2-induced NF-κB activation. In contrast, no clear difference was observed when NF-κB-dependent reporter gene expression was induced by NIK or more directly by overexpression of the p65 subunit of NF-κB (FIG. 8, FIG. 9). These results suggest that ABIN inhibits TNF-induced NF-κB activation at a level preceding the activation of the NIK-IκB kinase steps, for example at the level of TRAF2 in the TNF-receptor complex.

As members of the TRAF family mediate NF-κB activation by several other stimuli, including IL-1, lymphotoxin β, CD30 and CD40 (Rothe et al., 1995; Cao et al., 1996; Nakano et al., 1996; Aizawa et al., 1997; Ishada et al., 1996), ABIN might have the potential to inhibit NF-κB activation in response to a wide range of inducers. Therefore, drugs that mimic the activity of ABIN are likely to have therapeutic value in inflammatory and neurodegenerative diseases as well as in cancer and AIDS.

Example 7

Cell Transfection, Co-immunoprecipitation and Western Blotting.

$2\times10^6$ human embryonic kidney 293T cells were plated on 10 cm Petri dishes and transiently transfected by calcium phosphate-DNA coprecipitation. 24 hours after transfection, cells were lysed in 500 l of lysis buffer (50 mM Hepes pH 7.6, 250 mM NaCl, 0.1% Nonidet P-40 and 5 mM EDTA). Lysates were incubated with 5 l of rabbit anti-GFP antibody (Clontech) and immunocomplexes were immobilized on protein A-Trisacryl (Pierce). The latter were washed twice with lysis buffer and twice with lysis buffer containing 1M NaCl. Coprecipitating proteins were separated by SDS-PAGE and analyzed by Western blotting with mouse anti-E-tag antibody (Pharmacia).

Example 8

NF-κB Dependent Reporter Gene Assay.

NF-κB activity was determined by the NF-κB dependent expression of a luciferase reporter gene. Therefore, 293T cells were plated in 6-well plates at $4\times10^5$ cells per well and transiently transfected by the calcium phosphate-DNA coprecipitation method. Each transfection contained 800 ng of the specific expression plasmids, as well as 100 ng of pNFconluc plasmid and 100 ng pUT651 plasmid. 24 hours after transfection, these transfectants were trypsinized and seeded on a 24-well plate. Another 24 hours later, cells were either stimulated with 1000 IU/ml hTNF or 7000 IU/ml IL-1 or left untreated. After 6 hours of stimulation, cells were lysed in 200 µl lysis buffer and analyzed for luciferase and β-galactosidase activity. Luciferase values (luc) are normalized with (β-galactosidase values (gal) and plotted as luc/gal.

Example 9

Site Specific Mutagenesis.

Site specific mutagenesis on ABIN was performed by overlap PCR reaction using primers which contain the desired mutations. The primers used were the mutation primers 5'-GAATACCAGGAGGCGCAGATCCAGCG-GCTCAATAAAGCTTTGGAGGAGGC-3' (SEQ ID NO:11), 5'-GTTGCTGAAAGAGGACGT-CAAAATCTTTGAAGAGG-3' (SEQ ID NO:12), 5'-GCAG-GTAAAAATCTTTGAAGAGAATGCCCA-GAGGGAACG-3' (SEQ ID NO:13), and 5'-GCAGGTAAAAATCTTTGAAGAGGACTTC-CAGAGGGAAC GGAGTGATGCGCAACGCATGCCCG-3' (SEQ ID NO:14), a forward primer located at the start codon and two reverse primers, one hybridizing in the 3' UTR and one in the coding region. The XhoI-BstEII fragment of wild type ABIN(54-647) in pCAGGS was exchanged with the same fragment of the PCR amplified mutated ABIN cDNA's.

Example 10

Binding of ABIN With A20 is Not Sufficient for its NF-κB Inhibiting Potential.

Figure 10:
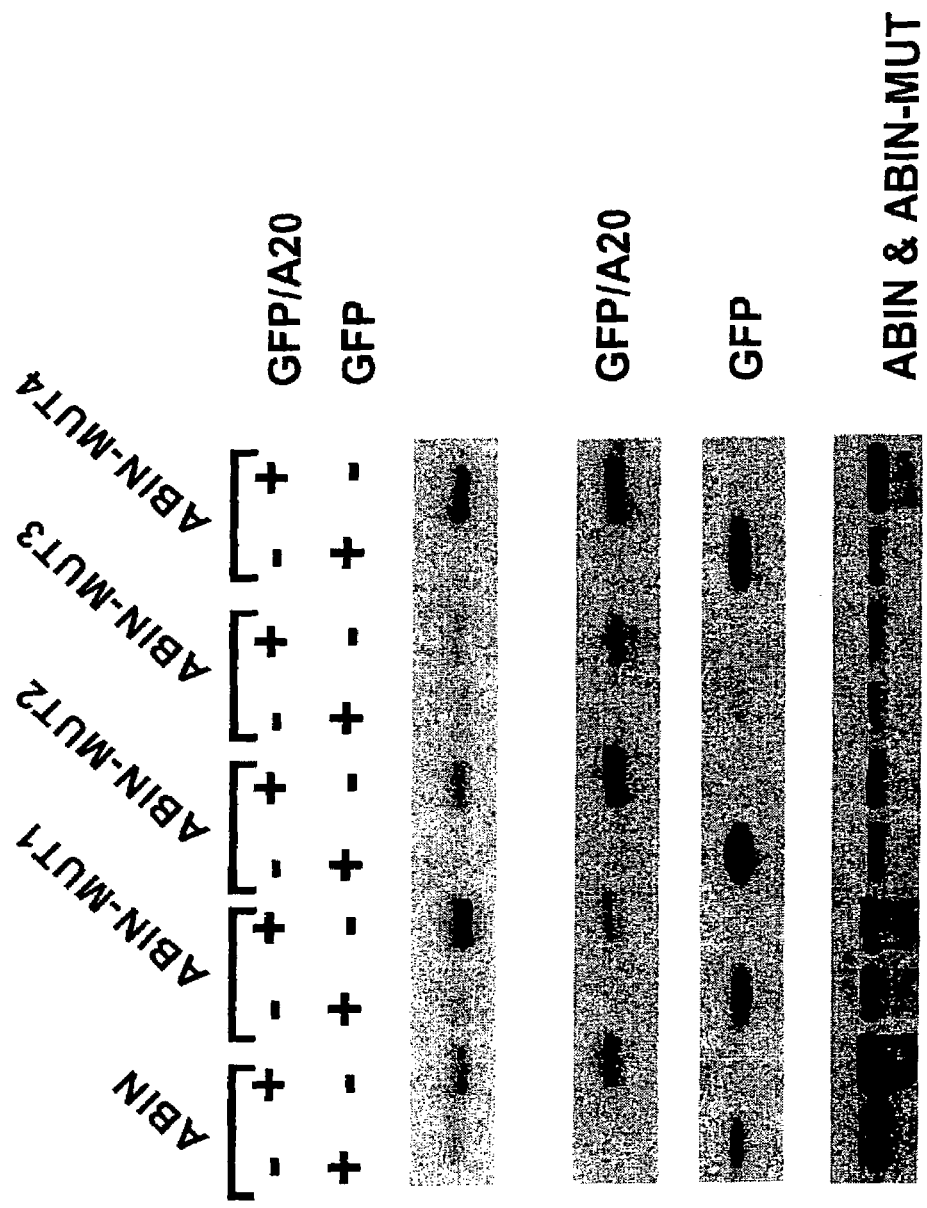
FIGS. 10, 11 and 12: As an overview, these figures illustrate the effect of site specific mutations in two regions of ABIN on its binding with A20 and on its inhibition of NF-κB activation.
Figure 11:
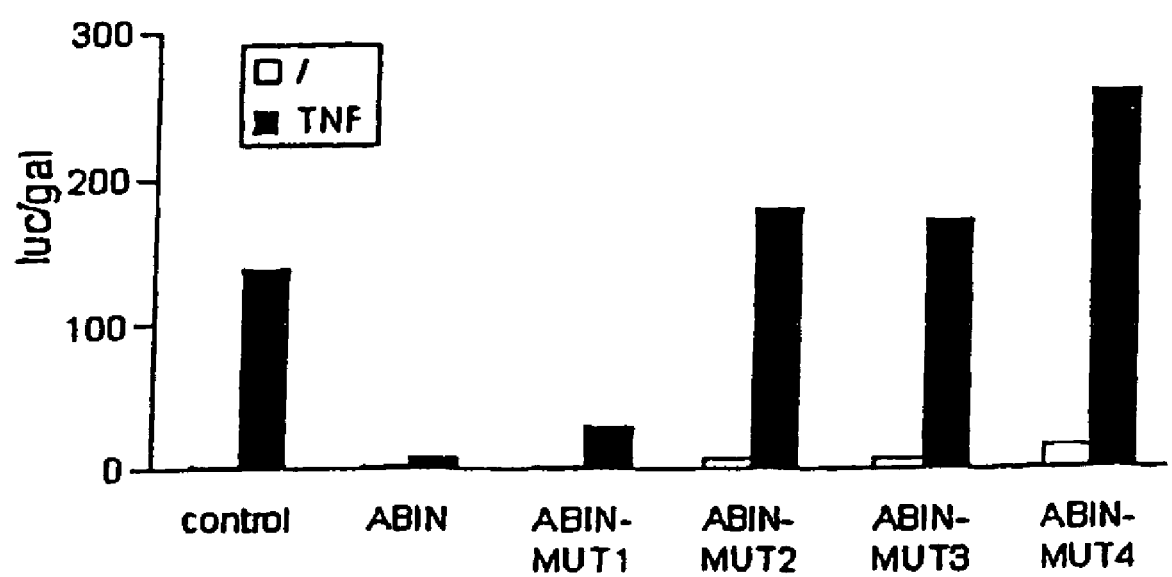
Figure 12:
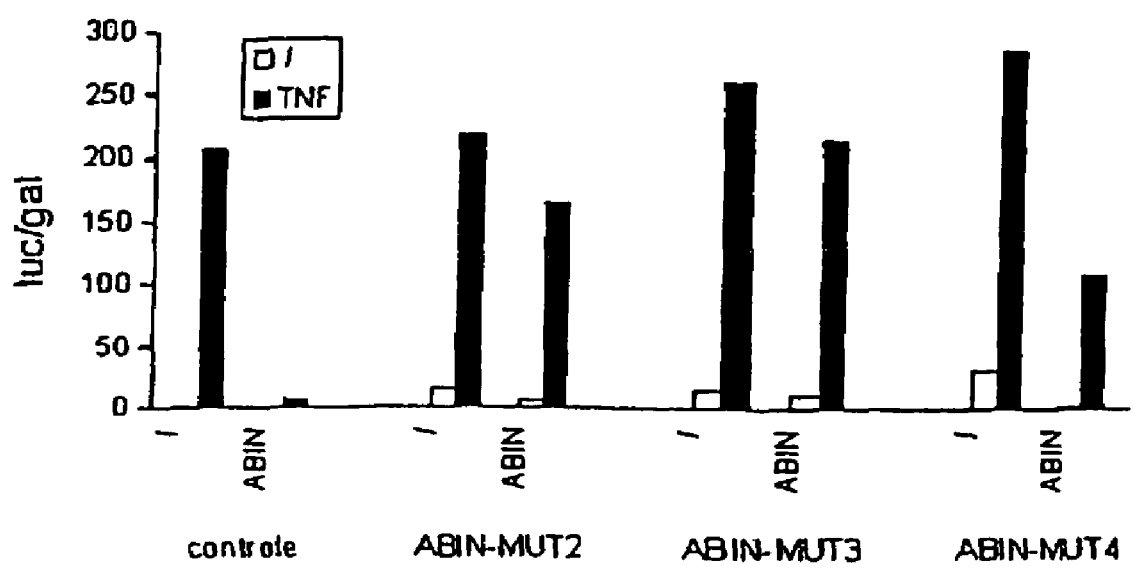

A two hybrid assay with A20 revealed another novel A20-binding protein which was also able to inhibit NF-κB activation upon overexpression. BLAST searches with this novel protein, named ABIN-2, revealed no homology with any known protein. However, by comparison of the protein sequence of ABIN-2 with ABIN, two boxes of 19 (AA 423-441) and 21 (AA 475-495) amino acids long with 68% and 67% homology were identified respectively. Therefore, the contribution of these regions to the binding with A20 and to the NF-κB inhibiting effects of ABIN were analyzed by site specific mutagenesis of a number of conserved amino acids. Co-immunoprecipitation analysis after transient overexpression of GFP or GFP/A20 together with wild type ABIN or its site specific mutants (ABIN-MUT1, ABIN-MUT2, ABIN-MUT3 and ABIN-MUT4) (SEQ ID NO:15, SEQ ID NO:16, SEQ ID NO:17 and SEQ ID NO:18 respectively) in 293T cells, showed that all of these mutants can still bind A20 (FIG. 10). On the other hand, point mutations in the second box (ABIN-MUT2, ABIN-MUT3 and ABIN-MUT4) completely abolished the ability of ABIN to block NF-κB activation upon stimulation of 293T cells with TNF, even when higher amounts of these expression plasmids were transfected. In contrast, the mutation in the first box (ABIN-MUT1) only slightly diminished the NF-κB inhibiting effect of ABIN (FIG. 11). Furthermore, point mutations in the second conserved motif dominantly interfered with the NF-κB inhibiting effect of wild type ABIN (FIG. 12). ABIN-MUT2 and ABIN-MUT3 exhibit a more potent function as dominant negative mutants of ABIN, compared to ABIN-MUT4. In these assays, comparable expression levels of the different mutants and of wild type ABIN were obtained as judged by Western blot analysis using anti-E tag antibody. These results suggest that the second conserved region is involved in the NF-κB inhibiting effects of ABIN, and that binding of ABIN with A20 as such is not sufficient for inhibition of NF-κB activation.

REFERENCES

Aizawa S, et al. Tumor necrosis factor receptor-associated factor (TRAF) 5 and TRAF2 are involved in CD30-mediated NF-κB activation. J Biol Chem. 272, 2042-2045. (1997)

Barnes P J, et al. Anti-inflammatory actions of steroids: molecular mechanisms. Trends Pharmacol Sci. 14(12): 436-441 (1993).

Barnes P J and Karin M. Nuclear factor-kappaB: a pivotal transcription factor in chronic inflammatory diseases. N Engl J Med. 336(15): 1066-1071 (1997).

Behl C, et al. Mechanism of amyloid beta protein induced neuronal cell death: current concepts and future perspectives. J Neural Transm Suppl. 49: 125-134 (1997).

Brand K, et al. Activated transcription factor nuclear factor-kappa B is present in the atherosclerotic lesion. J Clin Invest. 97(7): 1715-1722 (1996).

Brand K, et al. Dysregulation of monocytic nuclear factor-kappa B by oxidized low-density lipoprotein. Arterioscler Thromb Vasc Biol. 17(10): 1901-1909 (1997).

Cao Z, et al. TRAF6 is a signal transducer for interleukin-1. Nature. 383, 443-446. (1996)

De Valck D, et al. A20, an inhibitor of cell death, self-associates by its zinc finger domain. FEBS Lett. 384, 61-64. (1996)

De Valck D, et al. A20 inhibits NF-κB activation independently of binding to 14-3-3 proteins. Biochem Biophys Res Commun. 238, 590-594. (1997)

DiDonato J A, et al. A cytokine-responsive IκB kinase that activates the transcription factor NF-κB. Nature. 388, 548-554. (1997)

Dixit V M, et al. Tumor necrosis factor-alpha induction of novel gene products in human endothelial cells including a macrophage-specific chemotoxin. J Biol Chem. 265, 2973-2978. (1990)

Harris M. From negative factor to a critical role in virus pathogenesis : the changing fortunes of Nef. J Gen Virol. 77, 2379-2392. (1996)

Hsu H, et al. The TNF receptor 1-associated protein TRADD signals cell death and NF-κB activation. Cell. 81, 495-504. (1995)

Ishida T, et al. Identification of TRAF6, a novel tumor necrosis factor receptor-associated factor protein that mediates signaling from an amino-terminal domain of the CD40 cytoplasmic region. J Biol Chem. 271, 28745-28748. (1996)

Jaattela M, et al. A20 zinc finger protein inhibits TNF and IL-1 signaling. J Immunol. 156, 1166-1173. (1996)

Kaltschmidt C, et al. Transcription factor NF-kappa B is activated in microglia during experimental autoimmune encephalomyelitis. J Neuroimmunol. 55(1): 99-106. (1994)

Kimura A, et al. Detailed analysis of the mouse H-2Kb promoter: enhancer-like sequences and their role in the regulation of class I gene expression. Cell 44(2): 261-272. (1986)

Kopp E B and Ghosh S. Inhibition of NF-kappa B by sodium salicylate and aspirin. Science. 265(5174): 956-959. (1994)

Krikos A, et al. Transcriptional activation of the tumor necrosis factor alpha-inducible zinc finger protein, A20, is mediated by κB elements. J Biol Chem. 267, 17971-17976. (1992)

Luque I, et al. Rel/NF-kappa B and I kappa B factors in oncogenesis. Semin Cancer Biol. 8(2): 103-111. (1997)

Malanin N L, et al. MAP3K-related kinase involved in NF-κB induction by TNF, CD95 and IL-1. Nature. 385, 540-544 (1997)

Mosialos G. The role of Rel/NF-kappa B proteins in viral oncogenesis and the regulation of viral transcription. Semin Cancer Biol. 8(2): 121-129. (1997)

Nagase, T et al. Prediction of the coding sequences of unidentified human genes. III. The coding sequences of 40 new genes (KIAA0081-KIAA0120) deduced by analysis of cDNA clones from human cell line KG-1. DNA Res.2 (1), 37-43 (1995).

Nakano H, et al. TRAF5, an activator of NF-κB and putative signal transducer for the lymphotoxin-( receptor. J Biol Chem. 271, 14661-14664. (1996)

Niwa H. et al. Efficient selection for high-expression transfectants with a novel eukaryotic vector. Gene. 108, 193-199. (1991)

Opipari, A. W. et al. The A20 cDNA induced by tumor necrosis factor alpha encodes a novel type of zinc finger protein. J. Biol. Chem. 265, 14705-14708, (1990).

Pahl H L, et al. The immunosuppressive fungal metabolite gliotoxin specifically inhibits transcription factor NF-kappaB. J Exp Med. 183(4): 1829-1840. (1996)

Regnier C H, et al. Identification and characterization of an IκB kinase. Cell. 90, 373-383. (1997) Remick D G. Applied molecular biology of sepsis. J Crit Care. 10(4): 198-212. (1995)

Rothe M, et al. TRAF2-mediated activation of NF-κB by TNF receptor 2 and CD40. Science. 269, 1424-1427. (1995)

Rothe M, et al. A novel family of putative signal transducers associated with the cytoplasmic domain of the 75 kDa tumor necrosis factor receptor. Cell. 78, 681-692. (1994)

Schreck R, et al. Reactive oxygen intermediates as apparently widely used messengers in the activation of the NF-kappa B transcription factor and HIV-1. EMBO J. 10(8): 2247-2258 (1991)

Song H Y, et al. The tumor necrosis factor-inducible zinc finger protein A20 interacts with TRAF 1/TRAF2 and inhibits NF-κB activation. Proc Natl Acad Sci USA. 93, 6721-6725. (1996)

Tewari et al., Lymphoid expression and regulation of A20, an inhibitor of programmed cell death; J.Imnmunol. 1995, 154: 1699-1706.

Ting A T, et al. RIP mediates tumor necrosis factor receptor 1 activation of NF-κB but not Fas/APO-1-initiated apoptosis. EMBO J. 15, 6189-6196. (1996)

Vanden Berghe W. Et al. p38 and extracellular signal-regulated kinase mitogen-activated protein kinase pathways are required for nuclear factor-kappaB p65 transactivation mediated by tumor necrosis factor. J Biol Chem 273 (6): 3285-3290. (1998)

Wang P, et al. Interleukin (IL)-10 inhibits nuclear factor kappa B (NF kappa B) activation in human monocytes. Il-10 and IL-4 suppress cytokine synthesis by different mechanisms. J Biol Chem. 270(16): 9558-9563. (1995)

Woronicz J D, et al. IκB kinase-beta : NF-κB activation and complex formation with IκB kinase-α and NIK. Science. 278, 866-869.(1997)

Yeh W C. Et al. Early lethality, functional NF-kappaB activation, and increased sensitivity to TNF-induced cell death in TRAF2-deficient mice. Immunity 7(5): 715-725. (1997)

Zandi E, et al. The IκB kinase complex (IKK) contains two kinase subunits, IKKα and IKKβ, necessary for IκB phosphorylation and NF-κB activation. Cell. 91, 243-252. (1997)

What is claimed is:

1. A method of screening a compound for its ability to activate or suppress ABIN (A20-Binding Inhibitor of NF-κB activation) dependent NF-κB inhibition, said method comprising:
   a) combining a compound to be screened with a protein comprising ABIN amino acid consensus sequence of SEQ ID NO: 9 and having the ability to interact with protein A20,
   b) detecting an interaction between said compound and said protein,
   c) identifying compounds that interact with said protein,
   d) obtaining a cell line with that nucleic acid sequence encoding protein A20, nucleic acid sequence encoding said ABIN consensus sequence protein, and an NF-κB dependent reporter gene,
   e) administering at least one of TNF (tumor necrosis factor), IL-1 (interleukin-1), TPA (tissue plasminogen activator), TRADD (TNF receptor associated death domain), RIP (receptor interacting protein), TRAF2 (TNF receptor associated factor 2) to the cell line to induce activation of the NF-κB pathway,
   f) administering the detected compounds to said cell line, and
   g) determining if the administration of the detected compounds alter NF-κB dependent reporter gene expression, wherein an increase in expression indicates that the detected compounds suppress ABIN dependent NF-κB inhibition and a decrease in expression indicates that the compounds activate ABIN dependent NF-κB inhibition.

2. The method according to claim 1, wherein detecting an interaction between said compound and said protein comprises using either a two-hybrid assay or a co-immunoprecipitation assay.

3. A method of screening a compound for its ability to activate or suppress ABIN (A20-Binding Inhibitor of NF-κB activation) dependent NF-κB inhibition, said method comprising:
   a) combining a compound to be screened with a protein comprising ABIN amino acid consensus sequence of SEQ ID NO:9 and having the ability to inhibit NF-κB activation,
   b) detecting an interaction between said compound and said protein,
   c) identifying compounds that interact with said protein,
   d) obtaining a cell line with a nucleic acid sequence encoding said ABIN consensus sequence protein and an NF-κB dependent reporter gene,
   e) administering to the cell line an inducer of the NF-κB pathway, wherein the induction of the NF-κB pathway is inhibitable by said ABIN consensus sequence protein,
   f) administering one of the detected compounds to said cell line, and
   g) determining if the administration of the detected compound alters NF-κB dependent reporter gene expression, wherein an increase in expression indicates that the detected compound suppresses ABIN dependent NF-κB inhibition and a decrease in expression indicates that the detected compound activates ABiN dependent NF-κB inhibition.

4. The method according to claim 3, wherein obtaining a cell line comprises obtaining a cell line including a nucleic acid sequence encoding protein A20.

5. The method according to claim 3, wherein the inducer of the NF-κB pathway comprises at least one of TNF (tumor necrosis factor), IL-1 (interleukin-1), TPA (tissue plasminogen activator), TRADD (TNF receptor associated death domain), RIP (receptor interacting protein), or TRAF2 (TNF receptor associated factor 2).

6. A method of screening a compound for its ability to activate or suppress ABIN (A20-Binding Inhibitor of NF-κB activation) dependent NF-κB inhibition, said method comprising:
   a) combining a compound to be screened with a protein comprising ABIN amino acid consensus sequence of SEQ ID NO:9 and having the ability to inhibit NF-κB activation,
   b) detecting an interaction between said compound and said protein,
   c) identifying compounds that interact with said protein,
   d) obtaining a cell line with a nucleic acid sequence encoding said ABIN consensus sequence protein, an NF-κB dependent reporter gene, and a NF-κB pathway inducible by at least one of TNF (tumor necrosis factor), IL-1 (interleukin-1), TPA (tissue plasminogen activator), TRADD (TNF receptor associated death domain), RIP (receptor interacting protein), or TRAF2 (TNF receptor associated factor 2),
   e) inducing activation of the NF-κB pathway of said cell line,
   f) administering one of the detected compounds to said cell line, and
   g) determining if the administration of the detected compound alters NF-κB dependent reporter gene expression, wherein an increase in expression indicates that the detected compound suppresses ABIN dependent NF-κB inhibition and a decrease in expression indicates that the detected compound activates ABIN dependent NF-κB inhibition.

* * * * *

UNITED STATES PATENT AND TRADEMARK OFFICE
CERTIFICATE OF CORRECTION

PATENT NO. : 7,414,026 B2  Page 1 of 1
APPLICATION NO. : 10/680998
DATED : August 19, 2008
INVENTOR(S) : Rudi Beyaert, Karen Heyninck and Walter Fiers It is certified that error appears in the above-identified patent and that said Letters Patent is hereby corrected as shown below:

On the title page:
In ITEM (56) References Cited
OTHER PUBLICATIONS
Page 1
($1^{st}$ line of the $2^{nd}$ entry)  change "zzzzzinc" to --zinc--

COLUMN 20, LINE 7, change "Regnier C H," to --Regnier CH,--
COLUMN 20, LINE 8, change "Remick D G." to --Remick DG.--
COLUMN 20, LINE 23, change "TRAF 1/TRAF2 to --TRAF1/TRAF2--

Signed and Sealed this
First Day of March, 2011

David J. Kappos
*Director of the United States Patent and Trademark Office*